US011634505B2

(12) United States Patent
Smith et al.

(10) Patent No.: US 11,634,505 B2
(45) Date of Patent: Apr. 25, 2023

(54) ANTIBODIES TO MATRIX METALLOPROTEINASE 9

(71) Applicant: Gilead Sciences, Inc., Foster City, CA (US)

(72) Inventors: Victoria Smith, Burlingame, CA (US); Scott McCauley, San Francisco, CA (US)

(73) Assignee: Gilead Sciences, Inc., Foster City, CA (US)

(*) Notice: Subject to any disclaimer, the term of this patent is extended or adjusted under 35 U.S.C. 154(b) by 272 days.

(21) Appl. No.: 17/017,491

(22) Filed: Sep. 10, 2020

(65) Prior Publication Data

US 2021/0054101 A1 Feb. 25, 2021

Related U.S. Application Data

(60) Continuation of application No. 16/245,169, filed on Jan. 10, 2019, now Pat. No. 10,800,857, which is a continuation of application No. 15/376,232, filed on Dec. 12, 2016, now abandoned, which is a division of application No. 14/382,301, filed as application No. PCT/US2012/027160 on Feb. 29, 2012, now Pat. No. 9,550,836.

(51) Int. Cl.
| | |
|---|---|
| *C07K 16/40* | (2006.01) |
| *C12N 9/64* | (2006.01) |
| *G01N 33/573* | (2006.01) |
| *A61K 39/00* | (2006.01) |

(52) U.S. Cl.
CPC ............ *C07K 16/40* (2013.01); *C12N 9/6491* (2013.01); *C12Y 304/24035* (2013.01); *G01N 33/573* (2013.01); *A61K 2039/505* (2013.01); *A61K 2039/54* (2013.01); *A61K 2039/545* (2013.01); *C07K 2317/24* (2013.01); *C07K 2317/34* (2013.01); *C07K 2317/56* (2013.01); *C07K 2317/565* (2013.01); *C07K 2317/76* (2013.01); *C07K 2317/92* (2013.01); *G01N 2333/96494* (2013.01)

(58) Field of Classification Search
CPC .................................................... C07K 16/40
See application file for complete search history.

(56) References Cited

U.S. PATENT DOCUMENTS

| | | | |
|---|---|---|---|
| 6,632,927 | B2 | 10/2003 | Adair et al. |
| 8,377,443 | B2 | 2/2013 | McCauley et al. |
| 8,501,916 | B2 | 8/2013 | McCauley et al. |
| 9,120,863 | B2 | 9/2015 | McCauley et al. |
| 9,260,532 | B2 | 2/2016 | McCauley et al. |
| 9,550,836 | B2 | 1/2017 | Smith et al. |
| 9,732,156 | B2 | 8/2017 | Adamkewicz et al. |
| 10,800,857 | B2 | 10/2020 | Smith et al. |
| 2013/0224210 | A1 | 8/2013 | Adamkewicz et al. |
| 2015/0140580 | A1 | 5/2015 | Smith et al. |
| 2017/0183421 | A1 | 6/2017 | Smith et al. |
| 2018/0002446 | A1 | 1/2018 | Adamkewicz et al. |

FOREIGN PATENT DOCUMENTS

| | | |
|---|---|---|
| JP | 2015-514394 A | 5/2015 |
| WO | WO-2001/004157 A2 | 1/2001 |
| WO | WO-2004/022096 A1 | 3/2004 |
| WO | WO-2007/094842 A2 | 8/2007 |
| WO | WO-2008/154439 A1 | 12/2008 |
| WO | WO-2009/111450 A2 | 9/2009 |
| WO | WO-2009/111508 A2 | 9/2009 |
| WO | WO-2010/048432 A1 | 4/2010 |
| WO | WO-2010/059543 A1 | 5/2010 |
| WO | WO-2011/092700 A1 | 8/2011 |
| WO | WO-2012/027721 A2 | 3/2012 |
| WO | WO-2013/130078 A1 | 9/2013 |
| WO | WO-2013/130905 A1 | 9/2013 |

OTHER PUBLICATIONS

Beiboer, S.H.W., et al. (2000). "Guided Selection of a Pan Carcinoma Specific Antibody Reveals Similar Binding Characteristics yet Structural Divergence Between the Original Murine Antibody and its Human Equivalent," J. Mol. Biol. 296:833-849.

Carter, P.J. (May 2006, e-pub. Apr. 7, 2006). "Potent Antibody Therapeutics by Design," Nature Reviews 6(7):343-357.

Colby, D. et al. (Dec. 21, 2004, e-pub. Dec. 14, 2004). "Potent Inhibition of Huntingtin Aggregation and Cytotoxicity by a Disulfide Bond-Free Single-Domain Intracellular Antibody," PNAS USA 101(51):17616-17621.

Davies, J. et al. (1996). "Affinity Improvement of Single Antibody VH Domains: Residues in All Three Hypervariable Regions Affect Antigen Binding," Immunotechnology 2(3):169-179.

Holt, L.J. et al. (2003). "Domain Antibodies: Proteins for Therapy," Trends in Biotechnology 21(11):484-490.

Hu, J. et al. (2004). "Inhibitors of Gelatinase B/Matrix Metalloproteinase-9 Activity Comparison of a Peptidomimetic and Polyhistidine With Single-Chain Derivatives of a Neutralizing Monoclonal Antibody," Biochem. Pharmacol. 67(5):1001-1009.

Janeway, C.A. Jr., et al. (1997). "Structure of the Antibody Molecule and Immunoglobulin Genes" Chapter 3 in Immunobiology, Third Edition, Garland Publications, Inc., pp. 3:1-3:11.

Kimka, A. et al. (2000). Human Ant-CD30 Recombinant Antibodies by Guided Phage Antibody Selection Using Cell Panning, British Journal of Cancer 83(2):252-260.

Martens, E. et al. (2007). "A Monoclonal Antibody Inhibits Gelatinase B/MMP-9 by Selective Binding to Part of the Catalytic Domain and Not to the Fibronectin or Zinc Binding Domains," Biochim Biophys Acta 1770(2):178-186.

(Continued)

*Primary Examiner* — Prema M Mertz

(57) ABSTRACT

The present disclosure provides compositions and methods of use involving binding proteins, e.g., antibodies and antigen-binding fragments thereof, that bind to the matrix metalloproteinase-9 (MMP9) protein (MMP9 is also known as gelatinase-B), such as where the binding proteins comprise an immunoglobulin (Ig) heavy chain (or functional fragment thereof) and an Ig light chain (or functional fragment thereof).

13 Claims, 4 Drawing Sheets

Specification includes a Sequence Listing.

(56) References Cited

OTHER PUBLICATIONS

Masat, L., et al., "A Simpler Sort of Antibody (Light Chain Monomer/Nevus Antigen/Melanoma)," Proc. Natl. Acad. Sci. USA 91:893-896 (1994).
Panka, D.J. et al. (May 1988). "Variable Region Framework Differences Result in Decreased or Increased Affinity of Variant Anti-Digoxin Antibodies," Proc. Natl. Acad. Sci. USA 85:3080-3084.
Rader, C. et al. (Jul. 1998). "A Phage Display Approach for Rapid Antibody Humanization: Designed Combinatorial V Gene Libraries," *Proc. Natl. Acad. Sci.* 95:8910-8915.
Ramos-Desimone et al., "Inhibition of Matrix Metalloproteinase 9 Activation by a Specific Monoclonal Antibody", Hybridoma (1993) 12(4):349-363.
Rudikoff et al. (Mar. 1982). "Single Amino Acid Substitution Altering Antigen-Binding Specificity", *Proc. Natl. Acad. Sci. USA* 79:1979-1983.
Wark, K.L. et al. (2006). "Latest Technologies for the Enhancement of Antibody Affinity," Adv Drug Deliv Rev. 58(5-6):657-670.
Xu, J.L. et al. (Jul. 2000). "Diversity in the CDR3 Region of VH is Sufficient for Most Antibody Specificities," Immunity 13:37-45.
Australian Notice of Acceptance dated Aug. 9, 2016, for Patent Application No. 2012318302, filed Feb. 29, 2012, 4 pages (includes allowed claims).
Australian Office Action dated Aug. 21, 2018, for Patent Application No. 2017261626, filed Feb. 29, 2012, 6 pages.
Australian Office Action dated Aug. 21, 2018, for Patent Application No. 2017216508, filed Feb. 29, 2012, 5 pages.
Australian Office Action dated Nov. 13, 2014, for Application No. 2012318302, filed Feb. 29, 2012, 3 pages.
Australian Office Action dated Nov. 6, 2015, Application No. 2012318302, filed Feb. 29, 2012, 4 pages.
Australian Office Action dated Aug. 5, 2016, for Patent Application No. 2015242967, filed Feb. 29, 2012, 4 pages.
Canadian Office Action dated Jan. 31, 2018, for Patent Application No. 2,865,530, filed Feb. 29, 2012, 6 pages.
Chilean Office Action dated Aug. 17, 2015, for Patent Application No. 2282-2014, filed Feb. 29, 2012, 3 pages (and Agent's summary).
Chilean Office Action Report dated May 31, 2016, for Patent Application No. 2282-2014, filed Feb. 29, 2012, 17 pages Agent Summary in English.
Chinese Office Action dated Mar. 2, 2016, for Patent Application No. 201280072749.6, filed Feb. 29, 2012, 13 pages (includes English translation).
Colombian Office Action dated Jul. 7, 2015, for Patent Application No. 14-190.943, filed Feb. 29, 2012, 11 pages (English translation only).
Eurasian (First) Office Action dated Nov. 10, 2014, for Patent Application No. 201491575, filed Feb. 29, 2012, 5 pages includes English translation.
Eurasian (Second) Office Action, for Patent Application No. 201491575/28, filed Feb. 29, 2012, 1 page non-English, 2 pages English translation and claims.
European Office Action dated Aug. 2, 2018, for Patent Application No. 12708473.9, filed Feb. 29, 2012, 4 pages.
European Office Action dated Feb. 2, 2017, for Patent Application No. 12708473.9, filed Feb. 29, 2012, 3 pages.
European Office Action dated Jan. 18, 2016, for Patent Application No. 12708473.9, filed Feb. 29, 2012, 6 pages.
European Office Action dated Jul. 12, 2016, for Patent Application No. 12708473.9, filed Feb. 29, 2012, 3 pages.
European Office Action dated Nov. 25, 2014, for Patent Application No. 12708473.9, filed Feb. 29, 2012, 2 pages.
European Office Action dated Sep. 25, 2017, for Patent Application No. 12708473.9, filed Feb. 29, 2012, 3 pages.
European Office Action Response to Communication pursuant to Rules 161(1) and 162 (EPC) issued by the European Patent Office for Application No. 12708473.9, dated May 7, 2015, 1 page.

Indian Office Action dated May 13, 2019, for Patent Application No. 8011/DELN/2014, filed Feb. 29, 2012, 6 pages.
International Preliminary Report on Patentability for International Patent Application No. PCT/US2011/049448, dated Mar. 5, 2013.
International Search Report and Written Opinion for International Patent Application No. PCT/US2011/049448, dated Jun. 22, 2012.
International Preliminary Report on Patentability for International Patent Application No. PCT/US2012/027160, dated Mar. 26, 2014, 11 pages.
International Search Report and Written Opinion of the International Searching Authority for International Patent Application No. PCT/US2012/027160, dated Nov. 8, 2012.
International Preliminary Report on Patentability for International Patent Application No. PCT/US2013/028456, dated Sep. 2, 2014 10 pages.
International Search Report and Written Opinion of the International Searching Authority for International Patent Application No. PCT/US2013/028456, dated Jul. 26, 2013.
Israeli Office Action dated Jan. 24, 2016, for Patent Application No. 234304, filed Feb. 29, 2012, 3 pages (English translation only).
Japanese Arguments filed on Mar. 14. 2016 for Patent Application No. 2014-559872, filed. Feb. 29, 2012, 15 pages.
Japanese Office Action dated Aug. 1, 2017, for Patent Application No. 2016-049456, filed Mar. 14, 2016, 12 pages (including English translation).
Japanese Office Action dated Dec. 15, 2015 for Patent Application No. 2014-559872, filed Feb. 29, 2012, 6 pages (and 9 page English translation).
Japanese Office Action dated Dec. 15, 2016, for Patent Application No. 2016-049456, filed Mar. 14, 2016, 13 pages (including English translation).
Japanese Office Action dated Jul. 25, 2016, for Patent Application No. 2014-559872, filed Feb. 29, 2012, 3 pages Non-English and 6 page English translation.
Japanese Office Action dated Jul. 25, 2018, for Patent Application No. 2016-049456, filed Mar. 14, 2016, 11 pages (including English translation).
Mexican Application No. MX/a/2014/010449, Office Action dated Aug. 2, 2017, 3 pages. English translation.
New Zealand Office Action dated Feb. 25, 2020, for Patent Application No. 726487, filed Nov. 18, 2016, 2 pages.
New Zealand Notice of Acceptance dated Feb. 2, 2017, for Patent Application No. 629888, filed Feb. 29, 2012, 1 page.
New Zealand Office Action dated Dec. 16, 2016, for Patent Application No. 726487, filed Nov. 18, 2016, 4 pages.
New Zealand Office Action dated Dec. 16, 2016, Patent Application No. 629888, filed Feb. 29, 2012, 2 pages.
New Zealand Office Action dated May 25, 2015, for Patent Application No. 629888, filed Feb. 29, 2012, 3 pages.
Salvadorian Office Action dated Aug. 24, 2017, for Patent Application No. E-4798-2014, filed Aug. 29, 2014, 16 pages (with English translation).
Singapore Office Action dated Nov. 29, 2016 for Patent Application No. 11201405305P, Feb. 29, 2012, 2 pages and 2 pages of claims.
South African Acceptance Letter for (Grant) dated Nov. 3, 2015 (letter dated Jan. 8, 2016), (to issue Feb. 24, 2016) for Patent Application No. 2014/06319, Feb. 29, 2012, 1 page Agent letter.
Thai Office Action through email correspondence on May 18, 2016, (Formalities Only) for Patent Application No. 1401005043, Feb. 29, 2012, 15 pages (including response).
Thai Office Action Notice from Agent through email correspondence on Mar. 8, 2016 for Patent Application No. 1401005043, 4 pages, (e-mail—3 pages and one page English document).
U.S. Notice of Allowance dated Jun. 23, 2020, for U.S. Appl. No. 16/245,169, filed Jan. 10, 2019, 10 pages.
U.S. Restriction Requirement dated Mar. 30, 2020, for U.S. Appl. No. 16/245,169, filed Jan. 10, 2019, 7 pages.
U.S. Final Office Action dated Sep. 11, 2018, for U.S. Appl. No. 15/376,232, filed Dec. 12, 2016, 10 pages.
U.S. Office Action dated May 9, 2018, for U.S. Appl. No. 15/376,232, filed Dec. 12, 2016, 11 pages.
U.S. Restriction Requirement dated Aug. 30, 2017, for U.S. Appl. No. 15/376,232, filed Dec. 12, 2016, 7 pages.

(56) References Cited

OTHER PUBLICATIONS

U.S. Restriction Requirement dated May 23, 2016, for U.S. Appl. No. 14/382,301, filed Jan. 26, 2015, 8 pages.
Ukrainian Office Action (First), for Patent Application No. a201410545, filed Feb. 29, 2012, 8 pages (including English translation).
Vietnamese Office Action dated Dec. 19, 2014, for Patent Application No. 1-2014-03177, Feb. 29, 2012, 2 pages (with English translation).

Anti-MMP9 humanized heavy chains

```
AB0041   QVQLKESGPG LVAPSQSLSI TCTVSGFSLL SYGVHWVRQP PGKGLEWLGV
VH1      QVQLQESGPG LVKPSETLSL TCTVSGFSLL SYGVHWVRQP PGKGLEWLGV
VH2      QVQLQESGPG LVKPSETLSL TCTVSGFSLL SYGVHWVRQP PGKGLEWLGV
VH3      QVQLQESGPG LVKPSETLSL TCTVSGFSLL SYGVHWVRQP PGKGLEWLGV
VH4      QVQLQESGPG LVKPSETLSL TCTVSGFSLL SYGVHWVRQP PGKGLEWLGV

AB0041   IWTGGTTNYN SALMSRLSIS KDDSKSQVFL KMNSLQTDDT ATYYCARYYY
VH1      IWTGGTTNYN SALMSRLTIS KDDSKSTVYL KMNSLKTEDT ATYYCARYYY
VH2      IWTGGTTNYN SALMSRLTIS KDDSKNTVYL KMNSLKTEDT ATYYCARYYY
VH3      IWTGGTTNYN SALMSRETIS KDDSKNTVYL KMNSLKTEDT ATYYCARYYY
VH4      IWTGGTTNYN SALMSRETIS KDDSKNTLYL KMNSLKTEDT ATYYCARYYY

AB0041   GMDYWGQGTS VTVSS (SEQ ID NO: 3)
VH1      GMDYWGQGTS VTVSS (SEQ ID NO: 5)
VH2      GMDYWGQGTL VTVSS (SEQ ID NO: 6)
VH3      GMDYWGQGTL VTVSS (SEQ ID NO: 7)
VH4      GMDYWGQGTL VTVSS (SEQ ID NO: 8)
```

FIG. 1

Anti-MMP9 humanized light chains

```
AB0041  DIVMTQSHKF MSTSVGDRVS ITCKASQDVR NTVAWYQQKT GQSPKLLIYS
Vk1     DIVMTQSPSF LSASVGDRVT ITCKASQDVR NTVAWYQQKT GKAPKLLIYS
Vk2     DIVMTQSPSS LSASVGDRVT ITCKASQDVR NTVAWYQQKP GKAPKLLIYS
Vk3     DIQMTQSPSS LSASVGDRVT ITCKASQDVR NTVAWYQQKP GKAPKLLIYS
Vk4     DIQMTQSPSS LSASVGDRVT ITCKASQDVR NTVAWYQQKP GKAPKLLIYS

AB0041  SSYRNTGVPD RFTGSGSGTD FTFTISSVQA EDLAVYFCQQ HYITPYTFGG
Vk1     SSYRNTGVPD RFTGSGSGTD FTLTISSLQA EDVAVYFCQQ HYITPYTFGG
Vk2     SSYRNTGVPD RFTGSGSGTD FTLTISSLQA EDVAVYFCQQ HYITPYTFGG
Vk3     SSYRNTGVPD RFSGSGSGTD FTLTISSLQA EDVAVYFCQQ HYITPYTFGG
Vk4     SSYRNTGVPD RFSGSGSGTD FTLTISSLQA EDVAVYYCQQ HYITPYTFGG

AB0041  GTKLEIK  (SEQ ID NO:4)
Vk1     GTKVEIK  (SEQ ID NO:9)
Vk2     GTKVEIK  (SEQ ID NO:10)
Vk3     GTKVEIK  (SEQ ID NO:11)
Vk4     GTKVEIK  (SEQ ID NO:12)
```

FIG. 2

Comparison between AB0041, M4, and M12 heavy and light chains

Light chains

```
          Signal Peptide                                              CDRL1                                           CDRL2
M4      MESQIQVFVFVFLWLSGVDGDIVMTQSHKFMFTSVGDRVSITCKASQDVRNTVAWYQQKTGQSPKLLIYSASYRNTGVPD
AB0041  MESQIQVFVFVFLWLSGVDGDIVMTQSHKFMSTSVGDRVSITCKASQDVRNTVAWYQQKTGQSPKLLIYSSSYRNTGVPD
M12     ........QVFVYMLLWLSGVDGDIVMTQSQKFMSTSVGDRVSVTCKASQNVGTNVAWYQQKPGQSPKALIYSASYRFSGVPD
                                         CDRL3                             kappa constant
M4      RFTGSISGTDFTFTISSVQAEDLALYYCQQHYSTPYTFGGGTKLEVKRADAAPTVSIFPPSTRDPRAN
AB0041  RFTGSGSGTDFTFTISSVQAEDLAVYFCQQHYITPYTFGGGTKLEIKRADAAPTVSIFPPSTRDPRAN
M12     RFTGSGSGTDFTLTISNVQSEDLAEYFCQQYNSYPYTFGGGTKLEIKRADAAPTVSIFPPSTRDPRAN
```

Light chains

```
          Signal Peptide                                              CDRL1                                           CDRL2
M4      MAVLVLFLCLVAFPSCVLSQVQLKESGPGLVAPSQSLSITCTVSGFSLLSYGVHWRQPPGKGLEWLGVIWTGGSTNYNS
AB0041  MAVLVLFLCLVAFPSCVLSQVQLKESGPGLVAPSQSLSITCTVSGFSLLSYGVHWRQPPGKGLEWLGVIWTGGTTNYNS
                         CDRL3                                       IgG2b constant
M4      ALMSRLSISKDDSKSQVFLKMNSLQTDDTAMYYCARYYYAMDYWGQGTSVTVSSAKTTPPSVYPLAPGCGDTTGSSVTLG
AB0041  ALMSRLSISKDDSKSQVFLKMNSLQTDDTAIYYCARYYYGMDYWGQGTSVTVSSAKTTPPSVYPLAPGCGDTTGSSVTLG

M4      CLVKGYFPESVTVTWNSGSL
AB0041  CLVKGYFPEPVTVTWNSGSL
```

FIG. 4

```
                        SEQUENCE LISTING

<160> NUMBER OF SEQ ID NOS: 58

<210> SEQ ID NO 1
<211> LENGTH: 470
<212> TYPE: PRT
<213> ORGANISM: Mus musculus
<220> FEATURE:
<221> NAME/KEY: CHAIN
<222> LOCATION: (1)...(470)
<223> OTHER INFORMATION: AB0041 heavy chain
<220> FEATURE:
<221> NAME/KEY: PEPTIDE
<222> LOCATION: (1)...(19)
<223> OTHER INFORMATION: signal peptide
<220> FEATURE:
<221> NAME/KEY: misc_feature
<222> LOCATION: (135)...(470)
<223> OTHER INFORMATION: IgG2b constant region

<400> SEQUENCE: 1

Met Ala Val Leu Val Leu Phe Leu Cys Leu Val Ala Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Leu Ser Tyr Gly Val His Trp Val Arg Gln Pro Pro Gly Lys Gly Leu
    50                  55                  60

Glu Trp Leu Gly Val Ile Trp Thr Gly Gly Thr Thr Asn Tyr Asn Ser
65                  70                  75                  80

Ala Leu Met Ser Arg Leu Ser Ile Ser Lys Asp Asp Ser Lys Ser Gln
                85                  90                  95

Val Phe Leu Lys Met Asn Ser Leu Gln Thr Asp Asp Thr Ala Ile Tyr
            100                 105                 110
```

-continued

```
Tyr Cys Ala Arg Tyr Tyr Gly Met Asp Tyr Trp Gly Gln Gly Thr
            115                 120                 125

Ser Val Thr Val Ser Ser Ala Lys Thr Thr Pro Pro Ser Val Tyr Pro
    130                 135                 140

Leu Ala Pro Gly Cys Gly Asp Thr Thr Gly Ser Ser Val Thr Leu Gly
145                 150                 155                 160

Cys Leu Val Lys Gly Tyr Phe Pro Glu Ser Val Thr Val Thr Trp Asn
                165                 170                 175

Ser Gly Ser Leu Ser Ser Ser Val His Thr Phe Pro Ala Leu Leu Gln
            180                 185                 190

Ser Gly Leu Tyr Thr Met Ser Ser Ser Val Thr Val Pro Ser Ser Thr
        195                 200                 205

Trp Pro Ser Gln Thr Val Thr Cys Ser Val Ala His Pro Ala Ser Ser
    210                 215                 220

Thr Thr Val Asp Lys Lys Leu Glu Pro Ser Gly Pro Ile Ser Thr Ile
225                 230                 235                 240

Asn Pro Cys Pro Pro Cys Lys Glu Cys His Lys Cys Pro Ala Pro Asn
                245                 250                 255

Leu Glu Gly Gly Pro Ser Val Phe Ile Phe Pro Pro Asn Ile Lys Asp
            260                 265                 270

Val Leu Met Ile Ser Leu Thr Pro Lys Val Thr Cys Val Val Val Asp
        275                 280                 285

Val Ser Glu Asp Asp Pro Asp Val Arg Ile Ser Trp Phe Val Asn Asn
    290                 295                 300

Val Glu Val His Thr Ala Gln Thr Gln Thr His Arg Glu Asp Tyr Asn
305                 310                 315                 320

Ser Thr Ile Arg Val Val Ser Ala Leu Pro Ile Gln His Gln Asp Trp
                325                 330                 335

Met Ser Gly Lys Glu Phe Lys Cys Lys Val Asn Asn Lys Asp Leu Pro
            340                 345                 350

Ser Pro Ile Glu Arg Thr Ile Ser Lys Ile Lys Gly Leu Val Arg Ala
        355                 360                 365

Pro Gln Val Tyr Ile Leu Pro Pro Pro Ala Glu Gln Leu Ser Arg Lys
    370                 375                 380

Asp Val Ser Leu Thr Cys Leu Val Val Gly Phe Asn Pro Gly Asp Ile
385                 390                 395                 400

Ser Val Glu Trp Thr Ser Asn Gly His Thr Glu Glu Asn Tyr Lys Asp
                405                 410                 415

Thr Ala Pro Val Leu Asp Ser Asp Gly Ser Tyr Phe Ile Tyr Ser Lys
            420                 425                 430

Leu Asp Ile Lys Thr Ser Lys Trp Glu Lys Thr Asp Ser Phe Ser Cys
        435                 440                 445

Asn Val Arg His Glu Gly Leu Lys Asn Tyr Tyr Leu Lys Lys Thr Ile
    450                 455                 460

Ser Arg Ser Pro Gly Lys
465                 470
```

<210> SEQ ID NO 2
<211> LENGTH: 234
<212> TYPE: PRT
<213> ORGANISM: Mus musculus
<220> FEATURE:
<221> NAME/KEY: CHAIN
<222> LOCATION: (1)...(234)
<223> OTHER INFORMATION: AB0041 light chain
<220> FEATURE:

```
<221> NAME/KEY: PEPTIDE
<222> LOCATION: (1)...(20)
<223> OTHER INFORMATION: signal peptide
<220> FEATURE:
<221> NAME/KEY: misc_feature
<222> LOCATION: (128)...(234)
<223> OTHER INFORMATION: kappa constant region

<400> SEQUENCE: 2

Met Glu Ser Gln Ile Gln Val Phe Val Phe Val Phe Leu Trp Leu Ser
1               5                   10                  15

Gly Val Asp Gly Asp Ile Val Met Thr Gln Ser His Lys Phe Met Ser
                20                  25                  30

Thr Ser Val Gly Asp Arg Val Ser Ile Thr Cys Lys Ala Ser Gln Asp
            35                  40                  45

Val Arg Asn Thr Val Ala Trp Tyr Gln Gln Lys Thr Gly Gln Ser Pro
    50                  55                  60

Lys Leu Leu Ile Tyr Ser Ser Ser Tyr Arg Asn Thr Gly Val Pro Asp
65                  70                  75                  80

Arg Phe Thr Gly Ser Gly Ser Gly Thr Asp Phe Thr Phe Thr Ile Ser
                85                  90                  95

Ser Val Gln Ala Glu Asp Leu Ala Val Tyr Phe Cys Gln Gln His Tyr
                100                 105                 110

Ile Thr Pro Tyr Thr Phe Gly Gly Gly Thr Lys Leu Glu Ile Lys Arg
            115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
                180                 185                 190

Tyr Ser Met Ser Ser Thr Leu Thr Leu Thr Lys Asp Glu Tyr Glu Arg
            195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 3
<211> LENGTH: 115
<212> TYPE: PRT
<213> ORGANISM: Mus musculus
<220> FEATURE:
<221> NAME/KEY: CHAIN
<222> LOCATION: (1)...(115)
<223> OTHER INFORMATION: variable region of the IgG2b heavy chain of
      AB0041
<220> FEATURE:
<221> NAME/KEY: misc_feature
<222> LOCATION: (26)...(35)
<223> OTHER INFORMATION: complementarity-determining region (CDR)
<220> FEATURE:
<221> NAME/KEY: misc_feature
<222> LOCATION: (50)...(65)
<223> OTHER INFORMATION: complementarity-determining region (CDR)
<220> FEATURE:
<221> NAME/KEY: misc_feature
<222> LOCATION: (98)...(104)
<223> OTHER INFORMATION: complementarity-determining region (CDR)

<400> SEQUENCE: 3
```

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Leu Ser Tyr
            20                  25                  30

Gly Val His Trp Val Arg Gln Pro Pro Gly Lys Gly Leu Glu Trp Leu
        35                  40                  45

Gly Val Ile Trp Thr Gly Gly Thr Thr Asn Tyr Asn Ser Ala Leu Met
    50                  55                  60

Ser Arg Leu Ser Ile Ser Lys Asp Asp Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Arg Tyr Tyr Tyr Gly Met Asp Tyr Trp Gly Gln Gly Thr Ser Val Thr
            100                 105                 110

Val Ser Ser
        115

<210> SEQ ID NO 4
<211> LENGTH: 107
<212> TYPE: PRT
<213> ORGANISM: Mus musculus
<220> FEATURE:
<221> NAME/KEY: CHAIN
<222> LOCATION: (1)...(107)
<223> OTHER INFORMATION: variable region of the kappa light chain of
      AB0041
<220> FEATURE:
<221> NAME/KEY: misc_feature
<222> LOCATION: (24)...(34)
<223> OTHER INFORMATION: complementarity-determining region (CDR)
<220> FEATURE:
<221> NAME/KEY: misc_feature
<222> LOCATION: (50)...(56)
<223> OTHER INFORMATION: complementarity-determining region (CDR)
<220> FEATURE:
<221> NAME/KEY: misc_feature
<222> LOCATION: (89)...(97)
<223> OTHER INFORMATION: complementarity-determining region (CDR)

<400> SEQUENCE: 4

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Arg Asn Thr
            20                  25                  30

Val Ala Trp Tyr Gln Gln Lys Thr Gly Gln Ser Pro Lys Leu Leu Ile
        35                  40                  45

Tyr Ser Ser Ser Tyr Arg Asn Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Phe Cys Gln Gln His Tyr Ile Thr Pro Tyr
                85                  90                  95

Thr Phe Gly Gly Gly Thr Lys Leu Glu Ile Lys
            100                 105

<210> SEQ ID NO 5
<211> LENGTH: 115
<212> TYPE: PRT
<213> ORGANISM: Artificial Sequence
<220> FEATURE:
<223> OTHER INFORMATION: synthetic construct
<220> FEATURE:
```

```
<221> NAME/KEY: VARIANT
<222> LOCATION: (1)...(115)
<223> OTHER INFORMATION: VH1 heavy chain variant

<400> SEQUENCE: 5

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Leu Ser Tyr
            20                  25                  30

Gly Val His Trp Val Arg Gln Pro Pro Gly Lys Gly Leu Glu Trp Leu
        35                  40                  45

Gly Val Ile Trp Thr Gly Gly Thr Thr Asn Tyr Asn Ser Ala Leu Met
    50                  55                  60

Ser Arg Leu Thr Ile Ser Lys Asp Asp Ser Lys Ser Thr Val Tyr Leu
65                  70                  75                  80

Lys Met Asn Ser Leu Lys Thr Glu Asp Thr Ala Ile Tyr Tyr Cys Ala
                85                  90                  95

Arg Tyr Tyr Tyr Gly Met Asp Tyr Trp Gly Gln Gly Thr Ser Val Thr
            100                 105                 110

Val Ser Ser
        115

<210> SEQ ID NO 6
<211> LENGTH: 115
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(115)
<223> OTHER INFORMATION: VH2 heavy chain variant

<400> SEQUENCE: 6

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Leu Ser Tyr
            20                  25                  30

Gly Val His Trp Val Arg Gln Pro Pro Gly Lys Gly Leu Glu Trp Leu
        35                  40                  45

Gly Val Ile Trp Thr Gly Gly Thr Thr Asn Tyr Asn Ser Ala Leu Met
    50                  55                  60

Ser Arg Leu Thr Ile Ser Lys Asp Asp Ser Lys Asn Thr Val Tyr Leu
65                  70                  75                  80

Lys Met Asn Ser Leu Lys Thr Glu Asp Thr Ala Ile Tyr Tyr Cys Ala
                85                  90                  95

Arg Tyr Tyr Tyr Gly Met Asp Tyr Trp Gly Gln Gly Thr Leu Val Thr
            100                 105                 110

Val Ser Ser
        115

<210> SEQ ID NO 7
<211> LENGTH: 115
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(115)
<223> OTHER INFORMATION: VH3 heavy chain variant
```

-continued

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Leu Ser Tyr
            20                  25                  30

Gly Val His Trp Val Arg Gln Pro Pro Gly Lys Gly Leu Glu Trp Leu
        35                  40                  45

Gly Val Ile Trp Thr Gly Gly Thr Thr Asn Tyr Asn Ser Ala Leu Met
    50                  55                  60

Ser Arg Phe Thr Ile Ser Lys Asp Asp Ser Lys Asn Thr Val Tyr Leu
65                  70                  75                  80

Lys Met Asn Ser Leu Lys Thr Glu Asp Thr Ala Ile Tyr Tyr Cys Ala
                85                  90                  95

Arg Tyr Tyr Tyr Gly Met Asp Tyr Trp Gly Gln Gly Thr Leu Val Thr
            100                 105                 110

Val Ser Ser
        115

<210> SEQ ID NO 8
<211> LENGTH: 115
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(115)
<223> OTHER INFORMATION: VH4 heavy chain variant

<400> SEQUENCE: 8

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Leu Ser Tyr
            20                  25                  30

Gly Val His Trp Val Arg Gln Pro Pro Gly Lys Gly Leu Glu Trp Leu
        35                  40                  45

Gly Val Ile Trp Thr Gly Gly Thr Thr Asn Tyr Asn Ser Ala Leu Met
    50                  55                  60

Ser Arg Phe Thr Ile Ser Lys Asp Asp Ser Lys Asn Thr Leu Tyr Leu
65                  70                  75                  80

Lys Met Asn Ser Leu Lys Thr Glu Asp Thr Ala Ile Tyr Tyr Cys Ala
                85                  90                  95

Arg Tyr Tyr Tyr Gly Met Asp Tyr Trp Gly Gln Gly Thr Leu Val Thr
            100                 105                 110

Val Ser Ser
        115

<210> SEQ ID NO 9
<211> LENGTH: 107
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(107)
<223> OTHER INFORMATION: Vk1 light chain variant

<400> SEQUENCE: 9

```
Asp Ile Val Met Thr Gln Ser Pro Ser Phe Leu Ser Ala Ser Val Gly
1               5                   10                  15

Asp Arg Val Thr Ile Thr Cys Lys Ala Ser Gln Asp Val Arg Asn Thr
            20                  25                  30

Val Ala Trp Tyr Gln Gln Lys Thr Gly Lys Ala Pro Lys Leu Leu Ile
        35                  40                  45

Tyr Ser Ser Ser Tyr Arg Asn Thr Gly Val Pro Asp Arg Phe Thr Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Phe Cys Gln Gln His Tyr Ile Thr Pro Tyr
                85                  90                  95

Thr Phe Gly Gly Gly Thr Lys Val Glu Ile Lys
            100                 105
```

```
<210> SEQ ID NO 10
<211> LENGTH: 107
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(107)
<223> OTHER INFORMATION: Vk2 light chain variant

<400> SEQUENCE: 10

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Val Arg Asn Thr
            20                  25                  30

Val Ala Trp Tyr Gln Gln Lys Pro Gly Lys Ala Pro Lys Leu Leu Ile
        35                  40                  45

Tyr Ser Ser Ser Tyr Arg Asn Thr Gly Val Pro Asp Arg Phe Thr Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Phe Cys Gln Gln His Tyr Ile Thr Pro Tyr
                85                  90                  95

Thr Phe Gly Gly Gly Thr Lys Val Glu Ile Lys
            100                 105
```

```
<210> SEQ ID NO 11
<211> LENGTH: 107
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(107)
<223> OTHER INFORMATION: Vk3 light chain variant

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Arg Asn Thr
            20                  25                  30

Val Ala Trp Tyr Gln Gln Lys Pro Gly Lys Ala Pro Lys Leu Leu Ile
        35                  40                  45
```

```
Tyr Ser Ser Tyr Arg Asn Thr Gly Val Pro Asp Arg Phe Ser Gly
        50                  55                  60

Ser Gly Ser Gly Thr Asp Phe Thr Leu Thr Ile Ser Ser Leu Gln Ala
 65                  70                  75                  80

Glu Asp Val Ala Val Tyr Phe Cys Gln Gln His Tyr Ile Thr Pro Tyr
                     85                  90                  95

Thr Phe Gly Gly Gly Thr Lys Val Glu Ile Lys
            100                 105
```

<210> SEQ ID NO 12
<211> LENGTH: 107
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (1)...(107)
<223> OTHER INFORMATION: Vk4 light chain variant

<400> SEQUENCE: 12

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Arg Asn Thr
                20                  25                  30

Val Ala Trp Tyr Gln Gln Lys Pro Gly Lys Ala Pro Lys Leu Leu Ile
            35                  40                  45

Tyr Ser Ser Tyr Arg Asn Thr Gly Val Pro Asp Arg Phe Ser Gly
        50                  55                  60

Ser Gly Ser Gly Thr Asp Phe Thr Leu Thr Ile Ser Ser Leu Gln Ala
 65                  70                  75                  80

Glu Asp Val Ala Val Tyr Tyr Cys Gln Gln His Tyr Ile Thr Pro Tyr
                     85                  90                  95

Thr Phe Gly Gly Gly Thr Lys Val Glu Ile Lys
            100                 105
```

<210> SEQ ID NO 13
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(10)
<223> OTHER INFORMATION: complementarity-determining region (CDR1) of
      heavy chain of anti-MMP9 antibody

<400> SEQUENCE: 13

```
Gly Phe Ser Leu Leu Ser Tyr Gly Val His
 1               5                  10
```

<210> SEQ ID NO 14
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(16)
<223> OTHER INFORMATION: complementarity-determining region (CDR2) of
      heavy chain of anti-MMP9 antibody

<400> SEQUENCE: 14

```
Val Ile Trp Thr Gly Gly Thr Thr Asn Tyr Asn Ser Ala Leu Met Ser
1               5                   10                  15

<210> SEQ ID NO 15
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(7)
<223> OTHER INFORMATION: complementarity-determining region (CDR3) of
      heavy chain of anti-MMP9 antibody

<400> SEQUENCE: 15

Tyr Tyr Tyr Gly Met Asp Tyr
1               5

<210> SEQ ID NO 16
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(11)
<223> OTHER INFORMATION: complementarity-determining region (CDR1) of
      light chain of anti-MMP9 antibody

<400> SEQUENCE: 16

Lys Ala Ser Gln Asp Val Arg Asn Thr Val Ala
1               5                   10

<210> SEQ ID NO 17
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(7)
<223> OTHER INFORMATION: complementarity-determining region (CDR2) of
      light chain of anti-MMP9 antibody

<400> SEQUENCE: 17

Ser Ser Ser Tyr Arg Asn Thr
1               5

<210> SEQ ID NO 18
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(9)
<223> OTHER INFORMATION: complementarity-determining region (CDR3) of
      light chain of anti-MMP9 antibody

<400> SEQUENCE: 18

Gln Gln His Tyr Ile Thr Pro Tyr Thr
1               5

<210> SEQ ID NO 19
<211> LENGTH: 345
```

```
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(345)
<223> OTHER INFORMATION: nucleotide sequence encoding VH1 heavy chain
      amino acid sequence

<400> SEQUENCE: 19
caggtgcagc tgcaggaatc cggccctggc ctggtcaagc cctccgagac actgtccctg      60
acctgcaccg tgtccggctt ctccctgctg tcctacggcg tgcactgggt ccgacagcct     120
ccagggaagg gcctggaatg gctgggcgtg atctggaccg gcggcaccac caactacaac     180
tccgccctga tgtcccggct gaccatctcc aaggacgact ccaagtccac cgtgtacctg     240
aagatgaact ccctgaaaac cgaggacacc gccatctact actgcgcccg gtactactac     300
ggcatggact actggggcca gggcacctcc gtgaccgtgt cctca                      345

<210> SEQ ID NO 20
<211> LENGTH: 345
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(345)
<223> OTHER INFORMATION: nucleotide sequence encoding VH2 heavy chain
      amino acid sequence

<400> SEQUENCE: 20
caggtgcagc tgcaggaatc cggccctggc ctggtcaagc cctccgagac actgtccctg      60
acctgcaccg tgtccggctt ctccctgctg tcctacggcg tgcactgggt ccgacagcct     120
ccaggcaaag gcctggaatg gctgggcgtg atctggaccg gcggcaccac caactacaac     180
tccgccctga tgtcccggct gaccatctcc aaggacgact ccaagaacac cgtgtacctg     240
aagatgaact ccctgaaaac cgaggacacc gccatctact actgcgcccg gtactactac     300
ggcatggact actggggcca gggcaccctg gtcaccgtgt cctca                      345

<210> SEQ ID NO 21
<211> LENGTH: 345
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(345)
<223> OTHER INFORMATION: nucleotide sequence encoding VH3 heavy chain
      amino acid sequence

<400> SEQUENCE: 21
caggtgcagc tgcaggaatc cggccctggc ctggtcaagc cctccgagac actgtccctg      60
acctgcaccg tgtccggctt ctccctgctg tcctacggcg tgcactgggt ccgacagcct     120
ccaggcaaag gcctggaatg gctgggcgtg atctggaccg gcggcaccac caactacaac     180
tccgccctga tgtcccggtt caccatctcc aaggacgact ccaagaacac cgtgtacctg     240
aagatgaact ccctgaaaac cgaggacacc gccatctact actgcgcccg gtactactac     300
ggcatggact actggggcca gggcaccctg gtcaccgtgt cctca                      345
```

<210> SEQ ID NO 22
<211> LENGTH: 345
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(345)
<223> OTHER INFORMATION: nucleotide sequence encoding VH4 heavy chain amino acid sequence

<400> SEQUENCE: 22

```
caggtgcagc tgcaggaatc cggccctggc ctggtcaagc cctccgagac actgtccctg      60
acctgcaccg tgtccggctt ctccctgctg tcctacggcg tgcactgggt ccgacagcct     120
ccaggcaaag gcctggaatg gctgggcgtg atctggaccg gcggcaccac caactacaac     180
tccgccctga gtgtccggtt caccatctcc aaggacgact ccaagaacac cctgtacctg     240
aagatgaact ccctgaaaac cgaggacacc gccatctact actgcgcccg gtactactac     300
ggcatggact actggggcca gggcaccctg gtcaccgtgt cctca                     345
```

<210> SEQ ID NO 23
<211> LENGTH: 321
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(321)
<223> OTHER INFORMATION: nucleotide sequence encoding Vk1 light chain amino acid sequence

<400> SEQUENCE: 23

```
gacatcgtga tgacccagtc ccccagcttc ctgtccgcct ccgtgggcga cagagtgacc      60
atcacatgca aggcctctca ggacgtgcgg aacaccgtgg cctggtatca gcagaaaacc     120
ggcaaggccc ccaagctgct gatctactcc tcctcctacc ggaacaccgg cgtgcccgac     180
cggtttaccg gctctggctc cggcaccgac tttaccctga ccatcagctc cctgcaggcc     240
gaggacgtgg ccgtgtactt ctgccagcag cactacatca cccctacac cttcggcgga     300 ggcaccaagg tggaaataaa a                                               321
```

<210> SEQ ID NO 24
<211> LENGTH: 321
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(321)
<223> OTHER INFORMATION: nucleotide sequence encoding Vk2 light chain amino acid sequence

<400> SEQUENCE: 24

```
gacatcgtga tgacccagtc ccctccagc ctgtccgcct ctgtgggcga cagagtgacc       60
atcacatgca aggcctctca ggacgtgcgg aacaccgtgg cctggtatca gcagaagccc     120
ggcaaggccc ccaagctgct gatctactcc tcctcctacc ggaacaccgg cgtgcccgac     180
cggtttaccg gctctggctc cggcaccgac tttaccctga ccatcagctc cctgcaggcc     240
gaggacgtgg ccgtgtactt ctgccagcag cactacatca cccctacac cttcggcgga     300 ggcaccaagg tggaaataaa a                                               321
```

<210> SEQ ID NO 25
<211> LENGTH: 321
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(321)
<223> OTHER INFORMATION: nucleotide sequence encoding Vk3 light chain
      amino acid sequence

<400> SEQUENCE: 25
gacatccaga tgacccagtc cccctccagc ctgtccgcct ctgtgggcga cagagtgacc     60
atcacatgca aggcctccca ggacgtgcgg aacaccgtgg cctggtatca gcagaagccc    120
ggcaaggccc ccaagctgct gatctactcc tcctcctacc ggaacaccgg cgtgcccgac    180
cggttctctg gctctggaag cggcaccgac tttaccctga ccatcagctc cctgcaggcc    240
gaggacgtgg ccgtgtactt ctgccagcag cactacatca ccccctacac cttcggcgga    300
ggcaccaagg tggaaataaa a                                              321

<210> SEQ ID NO 26
<211> LENGTH: 321
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(321)
<223> OTHER INFORMATION: nucleotide sequence encoding Vk4 light chain
      amino acid sequence

<400> SEQUENCE: 26
gacatccaga tgacccagtc cccctccagc ctgtccgcct ctgtgggcga cagagtgacc     60
atcacatgca aggcctctca ggacgtgcgg aacaccgtgg cctggtatca gcagaagccc    120
ggcaaggccc ccaagctgct gatctactcc tcctcctacc ggaacaccgg cgtgcccgac    180
cggttctctg gctctggaag cggcaccgac tttaccctga ccatcagctc cctgcaggcc    240
gaggacgtgg ccgtgtacta ctgccagcag cactacatca ccccctacac cttcggcgga    300
ggcaccaagg tggaaataaa a                                              321

<210> SEQ ID NO 27
<211> LENGTH: 707
<212> TYPE: PRT
<213> ORGANISM: Homo sapiens
<220> FEATURE:
<221> NAME/KEY: misc_feature
<222> LOCATION: (1)...(707)
<223> OTHER INFORMATION: matrix metalloproteinase 9 (MMP9)
<220> FEATURE:
<221> NAME/KEY: PEPTIDE
<222> LOCATION: (1)...(19)
<223> OTHER INFORMATION: signal peptide
<220> FEATURE:
<221> NAME/KEY: DOMAIN
<222> LOCATION: (38)...(98)
<223> OTHER INFORMATION: peptidoglycan binding domain
<220> FEATURE:
<221> NAME/KEY: SITE
<222> LOCATION: (98)...(99)
<223> OTHER INFORMATION: propeptide cleavage site
<220> FEATURE:
<221> NAME/KEY: DOMAIN
<222> LOCATION: (112)...(445)

```
<223> OTHER INFORMATION: Zn dependent metalloproteinase domain
<220> FEATURE:
<221> NAME/KEY: DOMAIN
<222> LOCATION: (223)...(271)
<223> OTHER INFORMATION: fibronectin type II domain (gelatin binding
      domain)
<220> FEATURE:
<221> NAME/KEY: DOMAIN
<222> LOCATION: (281)...(329)
<223> OTHER INFORMATION: fibronectin type II domain (gelatin binding
      domain)
<220> FEATURE:
<221> NAME/KEY: DOMAIN
<222> LOCATION: (340)...(388)
<223> OTHER INFORMATION: fibronectin type II domain (gelatin binding
      domain)
<220> FEATURE:
<221> NAME/KEY: misc_feature
<222> LOCATION: (400)...(411)
<223> OTHER INFORMATION: Zn binding region
<220> FEATURE:
<221> NAME/KEY: DOMAIN
<222> LOCATION: (521)...(565)
<223> OTHER INFORMATION: hemopexin-like domain
<220> FEATURE:
<221> NAME/KEY: DOMAIN
<222> LOCATION: (567)...(608)
<223> OTHER INFORMATION: hemopexin-like domain
<220> FEATURE:
<221> NAME/KEY: DOMAIN
<222> LOCATION: (613)...(659)
<223> OTHER INFORMATION: hemopexin-like domain
<220> FEATURE:
<221> NAME/KEY: DOMAIN
<222> LOCATION: (661)...(704)
<223> OTHER INFORMATION: hemopexin-like domain

<400> SEQUENCE: 27

Met Ser Leu Trp Gln Pro Leu Val Leu Val Leu Leu Val Leu Gly Cys
1               5                   10                  15

Cys Phe Ala Ala Pro Arg Gln Arg Gln Ser Thr Leu Val Leu Phe Pro
            20                  25                  30

Gly Asp Leu Arg Thr Asn Leu Thr Asp Arg Gln Leu Ala Glu Glu Tyr
        35                  40                  45

Leu Tyr Arg Tyr Gly Tyr Thr Arg Val Ala Glu Met Arg Gly Glu Ser
50                  55                  60

Lys Ser Leu Gly Pro Ala Leu Leu Leu Gln Lys Gln Leu Ser Leu
65                  70                  75                  80

Pro Glu Thr Gly Glu Leu Asp Ser Ala Thr Leu Lys Ala Met Arg Thr
                85                  90                  95

Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
        115                 120                 125

Ser Glu Asp Leu Pro Arg Ala Val Ile Asp Asp Ala Phe Ala Arg Ala
130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
        195                 200                 205

Leu Trp Ser Leu Gly Lys Gly Val Val Val Pro Thr Arg Phe Gly Asn
```

```
                210                 215                 220
Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
                260                 265                 270

Ser Glu Arg Leu Tyr Thr Arg Asp Gly Asn Ala Asp Gly Lys Pro Cys
            275                 280                 285

Gln Phe Pro Phe Ile Phe Gln Gly Gln Ser Tyr Ser Ala Cys Thr Thr
            290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
                340                 345                 350

Phe Leu Gly Lys Glu Tyr Ser Thr Cys Thr Ser Glu Gly Arg Gly Asp
            355                 360                 365

Gly Arg Leu Trp Cys Ala Thr Thr Ser Asn Phe Asp Ser Asp Lys Lys
            370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
                420                 425                 430

Lys Asp Asp Val Asn Gly Ile Arg His Leu Tyr Gly Pro Arg Pro Glu
            435                 440                 445

Pro Glu Pro Arg Pro Pro Thr Thr Thr Pro Gln Pro Thr Ala Pro
450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495

Pro Thr Ala Gly Pro Ser Thr Ala Thr Thr Val Pro Leu Ser Pro Val
                500                 505                 510

Asp Asp Ala Cys Asn Val Asn Ile Phe Asp Ala Ile Ala Glu Ile Gly
            515                 520                 525

Asn Gln Leu Tyr Leu Phe Lys Asp Gly Lys Tyr Trp Arg Phe Ser Glu
530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Pro Leu Ser
                565                 570                 575

Lys Lys Leu Phe Phe Phe Ser Gly Arg Gln Val Trp Val Tyr Thr Gly
                580                 585                 590

Ala Ser Val Leu Gly Pro Arg Arg Leu Asp Lys Leu Gly Leu Gly Ala
            595                 600                 605

Asp Val Ala Gln Val Thr Gly Ala Leu Arg Ser Gly Arg Gly Lys Met
            610                 615                 620

Leu Leu Phe Ser Gly Arg Arg Leu Trp Arg Phe Asp Val Lys Ala Gln
625                 630                 635                 640
```

```
Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
                660                 665                 670

Phe Cys Gln Asp Arg Phe Tyr Trp Arg Val Ser Ser Arg Ser Glu Leu
                675                 680                 685

Asn Gln Val Asp Gln Val Gly Tyr Val Thr Tyr Asp Ile Leu Gln Cys
                690                 695                 700

Pro Glu Asp
705

<210> SEQ ID NO 28
<211> LENGTH: 688
<212> TYPE: PRT
<213> ORGANISM: Homo sapiens
<220> FEATURE:
<221> NAME/KEY: misc_feature
<222> LOCATION: (1)...(688)
<223> OTHER INFORMATION: mature full-length matrix metalloproteinase 9
      (MMP9)

<400> SEQUENCE: 28

Ala Pro Arg Gln Arg Gln Ser Thr Leu Val Leu Phe Pro Gly Asp Leu
1               5                   10                  15

Arg Thr Asn Leu Thr Asp Arg Gln Leu Ala Glu Glu Tyr Leu Tyr Arg
                20                  25                  30

Tyr Gly Tyr Thr Arg Val Ala Glu Met Arg Gly Glu Ser Lys Ser Leu
            35                  40                  45

Gly Pro Ala Leu Leu Leu Leu Gln Lys Gln Leu Ser Leu Pro Glu Thr
        50                  55                  60

Gly Glu Leu Asp Ser Ala Thr Leu Lys Ala Met Arg Thr Pro Arg Cys
65                  70                  75                  80

Gly Val Pro Asp Leu Gly Arg Phe Gln Thr Phe Glu Gly Asp Leu Lys
                85                  90                  95

Trp His His Asn Ile Thr Tyr Trp Ile Gln Asn Tyr Ser Glu Asp
                100                 105                 110

Leu Pro Arg Ala Val Ile Asp Asp Ala Phe Ala Arg Ala Phe Ala Leu
                115                 120                 125

Trp Ser Ala Val Thr Pro Leu Thr Phe Thr Arg Val Tyr Ser Arg Asp
            130                 135                 140

Ala Asp Ile Val Ile Gln Phe Gly Val Ala Glu His Gly Asp Gly Tyr
145                 150                 155                 160

Pro Phe Asp Gly Lys Asp Gly Leu Leu Ala His Ala Phe Pro Pro Gly
                165                 170                 175

Pro Gly Ile Gln Gly Asp Ala His Phe Asp Asp Glu Leu Trp Ser
                180                 185                 190

Leu Gly Lys Gly Val Val Val Pro Thr Arg Phe Gly Asn Ala Asp Gly
            195                 200                 205

Ala Ala Cys His Phe Pro Phe Ile Phe Glu Gly Arg Ser Tyr Ser Ala
        210                 215                 220

Cys Thr Thr Asp Gly Arg Ser Asp Gly Leu Pro Trp Cys Ser Thr Thr
225                 230                 235                 240

Ala Asn Tyr Asp Thr Asp Asp Arg Phe Gly Phe Cys Pro Ser Glu Arg
                245                 250                 255

Leu Tyr Thr Arg Asp Gly Asn Ala Asp Gly Lys Pro Cys Gln Phe Pro
                260                 265                 270
```

```
Phe Ile Phe Gln Gly Gln Ser Tyr Ser Ala Cys Thr Thr Asp Gly Arg
    275                 280                 285

Ser Asp Gly Tyr Arg Trp Cys Ala Thr Thr Ala Asn Tyr Asp Arg Asp
    290                 295                 300

Lys Leu Phe Gly Phe Cys Pro Thr Arg Ala Asp Ser Thr Val Met Gly
305                 310                 315                 320

Gly Asn Ser Ala Gly Glu Leu Cys Val Phe Pro Phe Thr Phe Leu Gly
                325                 330                 335

Lys Glu Tyr Ser Thr Cys Thr Ser Glu Gly Arg Gly Asp Gly Arg Leu
            340                 345                 350

Trp Cys Ala Thr Thr Ser Asn Phe Asp Ser Asp Lys Lys Trp Gly Phe
        355                 360                 365

Cys Pro Asp Gln Gly Tyr Ser Leu Phe Leu Val Ala Ala His Glu Phe
    370                 375                 380

Gly His Ala Leu Gly Leu Asp His Ser Ser Val Pro Glu Ala Leu Met
385                 390                 395                 400

Tyr Pro Met Tyr Arg Phe Thr Glu Gly Pro Pro Leu His Lys Asp Asp
                405                 410                 415

Val Asn Gly Ile Arg His Leu Tyr Gly Pro Arg Pro Glu Pro Glu Pro
            420                 425                 430

Arg Pro Pro Thr Thr Thr Thr Pro Gln Pro Thr Ala Pro Pro Thr Val
        435                 440                 445

Cys Pro Thr Gly Pro Pro Thr Val His Pro Ser Glu Arg Pro Thr Ala
    450                 455                 460

Gly Pro Thr Gly Pro Pro Ser Ala Gly Pro Thr Gly Pro Pro Thr Ala
465                 470                 475                 480

Gly Pro Ser Thr Ala Thr Thr Val Pro Leu Ser Pro Val Asp Asp Ala
                485                 490                 495

Cys Asn Val Asn Ile Phe Asp Ala Ile Ala Glu Ile Gly Asn Gln Leu
            500                 505                 510

Tyr Leu Phe Lys Asp Gly Lys Tyr Trp Arg Phe Ser Glu Gly Arg Gly
        515                 520                 525

Ser Arg Pro Gln Gly Pro Phe Leu Ile Ala Asp Lys Trp Pro Ala Leu
    530                 535                 540

Pro Arg Lys Leu Asp Ser Val Phe Glu Glu Pro Leu Ser Lys Lys Leu
545                 550                 555                 560

Phe Phe Phe Ser Gly Arg Gln Val Trp Val Tyr Thr Gly Ala Ser Val
                565                 570                 575

Leu Gly Pro Arg Arg Leu Asp Lys Leu Gly Leu Gly Ala Asp Val Ala
            580                 585                 590

Gln Val Thr Gly Ala Leu Arg Ser Gly Arg Gly Lys Met Leu Leu Phe
        595                 600                 605

Ser Gly Arg Arg Leu Trp Arg Phe Asp Val Lys Ala Gln Met Val Asp
    610                 615                 620

Pro Arg Ser Ala Ser Glu Val Asp Arg Met Phe Pro Gly Val Pro Leu
625                 630                 635                 640

Asp Thr His Asp Val Phe Gln Tyr Arg Glu Lys Ala Tyr Phe Cys Gln
                645                 650                 655

Asp Arg Phe Tyr Trp Arg Val Ser Ser Arg Ser Glu Leu Asn Gln Val
            660                 665                 670

Asp Gln Val Gly Tyr Val Thr Tyr Asp Ile Leu Gln Cys Pro Glu Asp
        675                 680                 685
```

```
<210> SEQ ID NO 29
<211> LENGTH: 19
<212> TYPE: PRT
<213> ORGANISM: Homo sapiens

<400> SEQUENCE: 29

Met Ser Leu Trp Gln Pro Leu Val Leu Val Leu Val Leu Gly Cys
1               5                   10                  15

Cys Phe Ala

<210> SEQ ID NO 30
<211> LENGTH: 470
<212> TYPE: PRT
<213> ORGANISM: Mus musculus
<220> FEATURE:
<221> NAME/KEY: CHAIN
<222> LOCATION: (1)...(470)
<223> OTHER INFORMATION: M4 heavy chain (IgG2b)

<400> SEQUENCE: 30

Met Ala Val Leu Val Leu Phe Leu Cys Leu Val Ala Phe Pro Ser Cys
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Leu Ser Tyr Gly Val His Trp Val Arg Gln Pro Pro Gly Lys Gly Leu
    50                  55                  60

Glu Trp Leu Gly Val Ile Trp Thr Gly Gly Ser Thr Asn Tyr Asn Ser
65                  70                  75                  80

Ala Leu Met Ser Arg Leu Ser Ile Ser Lys Asp Asp Ser Lys Ser Gln
                85                  90                  95

Val Phe Leu Lys Met Asn Ser Leu Gln Thr Asp Asp Thr Ala Met Tyr
            100                 105                 110

Tyr Cys Ala Arg Tyr Tyr Tyr Ala Met Asp Tyr Trp Gly Gln Gly Thr
        115                 120                 125

Ser Val Thr Val Ser Ser Ala Lys Thr Thr Pro Pro Ser Val Tyr Pro
    130                 135                 140

Leu Ala Pro Gly Cys Gly Asp Thr Thr Gly Ser Ser Val Thr Leu Gly
145                 150                 155                 160

Cys Leu Val Lys Gly Tyr Phe Pro Glu Ser Val Thr Val Thr Trp Asn
                165                 170                 175

Ser Gly Ser Leu Ser Ser Ser Val His Thr Phe Pro Ala Leu Leu Gln
            180                 185                 190

Ser Gly Leu Tyr Thr Met Ser Ser Ser Val Thr Val Pro Ser Ser Thr
        195                 200                 205

Trp Pro Ser Gln Thr Val Thr Cys Ser Val Ala His Pro Ala Ser Ser
    210                 215                 220

Thr Thr Val Asp Lys Lys Leu Glu Pro Ser Gly Pro Ile Ser Thr Ile
225                 230                 235                 240

Asn Pro Cys Pro Pro Cys Lys Glu Cys His Lys Cys Pro Ala Pro Asn
                245                 250                 255

Leu Glu Gly Gly Pro Ser Val Phe Ile Phe Pro Pro Asn Ile Lys Asp
            260                 265                 270

Val Leu Met Ile Ser Leu Thr Pro Lys Val Thr Cys Val Val Val Asp
        275                 280                 285
```

Val Ser Glu Asp Asp Pro Asp Val Arg Ile Ser Trp Phe Val Asn Asn
290                 295                 300

Val Glu Val His Thr Ala Gln Thr Gln Thr His Arg Glu Asp Tyr Asn
305                 310                 315                 320

Ser Thr Ile Arg Val Val Ser Ala Leu Pro Ile Gln His Gln Asp Trp
                325                 330                 335

Met Ser Gly Lys Glu Phe Lys Cys Lys Val Asn Asn Lys Asp Leu Pro
                340                 345                 350

Ser Pro Ile Glu Arg Thr Ile Ser Lys Ile Lys Gly Leu Val Arg Ala
                355                 360                 365

Pro Gln Val Tyr Ile Leu Pro Pro Ala Glu Gln Leu Ser Arg Lys
370                 375                 380

Asp Val Ser Leu Thr Cys Leu Val Val Gly Phe Asn Pro Gly Asp Ile
385                 390                 395                 400

Ser Val Glu Trp Thr Ser Asn Gly His Thr Glu Glu Asn Tyr Lys Asp
                405                 410                 415

Thr Ala Pro Val Leu Asp Ser Asp Gly Ser Tyr Phe Ile Tyr Ser Lys
                420                 425                 430

Leu Asp Ile Lys Thr Ser Lys Trp Glu Lys Thr Asp Ser Phe Ser Cys
                435                 440                 445

Asn Val Arg His Glu Gly Leu Lys Asn Tyr Tyr Leu Lys Lys Thr Ile
450                 455                 460

Ser Arg Ser Pro Gly Lys
465                 470

<210> SEQ ID NO 31
<211> LENGTH: 234
<212> TYPE: PRT
<213> ORGANISM: Mus musculus
<220> FEATURE:
<221> NAME/KEY: CHAIN
<222> LOCATION: (1)...(234)
<223> OTHER INFORMATION: M4 light chain (kappa)

<400> SEQUENCE: 31

Met Glu Ser Gln Ile Gln Val Phe Val Phe Leu Trp Leu Ser
1               5                   10                  15

Gly Val Asp Gly Asp Ile Val Met Thr Gln Ser His Lys Phe Met Phe
                20                  25                  30

Thr Ser Val Gly Asp Arg Val Ser Ile Thr Cys Lys Ala Ser Gln Asp
                35                  40                  45

Val Arg Asn Thr Val Ala Trp Tyr Gln Gln Lys Thr Gly Gln Ser Pro
50                  55                  60

Lys Leu Leu Ile Tyr Ser Ala Ser Tyr Arg Asn Thr Gly Val Pro Asp
65                  70                  75                  80

Arg Phe Thr Gly Ser Ile Ser Gly Thr Asp Phe Thr Phe Thr Ile Ser
                85                  90                  95

Ser Val Gln Ala Glu Asp Leu Ala Leu Tyr Tyr Cys Gln Gln His Tyr
                100                 105                 110

Ser Thr Pro Tyr Thr Phe Gly Gly Gly Thr Lys Leu Glu Val Lys Arg
                115                 120                 125

Ala Asp Ala Ala Pro Thr Val Ser Ile Phe Pro Pro Ser Ser Glu Gln
                130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln

```
                    165                 170                 175
Asn Gly Val Leu Asn Ser Trp Thr Asp Gln Asp Ser Lys Asp Ser Thr
                180                 185                 190

Tyr Ser Met Ser Ser Thr Leu Thr Leu Thr Lys Asp Glu Tyr Glu Arg
            195                 200                 205

His Asn Ser Tyr Thr Cys Glu Ala Thr His Lys Thr Ser Thr Ser Pro
        210                 215                 220

Ile Val Lys Ser Phe Asn Arg Asn Glu Cys
225                 230

<210> SEQ ID NO 32
<211> LENGTH: 115
<212> TYPE: PRT
<213> ORGANISM: Mus musculus

<400> SEQUENCE: 32

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Leu Ser Tyr
            20                  25                  30

Gly Val His Trp Val Arg Gln Pro Pro Gly Lys Gly Leu Glu Trp Leu
        35                  40                  45

Gly Val Ile Trp Thr Gly Gly Ser Thr Asn Tyr Asn Ser Ala Leu Met
    50                  55                  60

Ser Arg Leu Ser Ile Ser Lys Asp Asp Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Tyr Tyr Tyr Ala Met Asp Tyr Trp Gly Gln Gly Thr Ser Val Thr
            100                 105                 110

Val Ser Ser
        115

<210> SEQ ID NO 33
<211> LENGTH: 107
<212> TYPE: PRT
<213> ORGANISM: Mus musculus

<400> SEQUENCE: 33

Asp Ile Val Met Thr Gln Ser His Lys Phe Met Phe Thr Ser Val Gly
1               5                   10                  15

Asp Arg Val Ser Ile Thr Cys Lys Ala Ser Gln Asp Val Arg Asn Thr
            20                  25                  30

Val Ala Trp Tyr Gln Gln Lys Thr Gly Gln Ser Pro Lys Leu Leu Ile
        35                  40                  45

Tyr Ser Ala Ser Tyr Arg Asn Thr Gly Val Pro Asp Arg Phe Thr Gly
    50                  55                  60

Ser Ile Ser Gly Thr Asp Phe Thr Phe Thr Ile Ser Ser Val Gln Ala
65                  70                  75                  80

Glu Asp Leu Ala Leu Tyr Tyr Cys Gln Gln His Tyr Ser Thr Pro Tyr
                85                  90                  95

Thr Phe Gly Gly Gly Thr Lys Leu Glu Val Lys
            100                 105

<210> SEQ ID NO 34
<211> LENGTH: 10
<212> TYPE: PRT
```

```
<213> ORGANISM: Mus musculus

<400> SEQUENCE: 34

Gly Phe Ser Leu Leu Ser Tyr Gly Val His
1               5                   10

<210> SEQ ID NO 35
<211> LENGTH: 10
<212> TYPE: PRT
<213> ORGANISM: Mus musculus

<400> SEQUENCE: 35

Val Ile Trp Thr Gly Gly Ser Thr Asn Tyr
1               5                   10

<210> SEQ ID NO 36
<211> LENGTH: 7
<212> TYPE: PRT
<213> ORGANISM: Mus musculus

<400> SEQUENCE: 36

Tyr Tyr Tyr Ala Met Asp Tyr
1               5

<210> SEQ ID NO 37
<211> LENGTH: 11
<212> TYPE: PRT
<213> ORGANISM: Mus musculus

<400> SEQUENCE: 37

Lys Ala Ser Gln Asp Val Arg Asn Thr Val Ala
1               5                   10

<210> SEQ ID NO 38
<211> LENGTH: 7
<212> TYPE: PRT
<213> ORGANISM: Mus musculus

<400> SEQUENCE: 38

Ser Ala Ser Tyr Arg Asn Thr
1               5

<210> SEQ ID NO 39
<211> LENGTH: 9
<212> TYPE: PRT
<213> ORGANISM: Mus musculus

<400> SEQUENCE: 39

Gln Gln His Tyr Ser Thr Pro Tyr Thr
1               5

<210> SEQ ID NO 40
<211> LENGTH: 229
<212> TYPE: PRT
<213> ORGANISM: Mus musculus
<220> FEATURE:
<221> NAME/KEY: CHAIN
<222> LOCATION: (1)...(229)
<223> OTHER INFORMATION: M12 kappa chain

<400> SEQUENCE: 40

Gln Val Phe Val Tyr Met Leu Leu Trp Leu Ser Gly Val Asp Gly Asp
1               5                   10                  15

Ile Val Met Thr Gln Ser Gln Lys Phe Met Ser Thr Ser Val Gly Asp
                20                  25                  30
```

```
Arg Val Ser Val Thr Cys Lys Ala Ser Gln Asn Val Gly Thr Asn Val
        35                  40                  45

Ala Trp Tyr Gln Gln Lys Pro Gly Gln Ser Pro Lys Ala Leu Ile Tyr
 50                  55                  60

Ser Ala Ser Tyr Arg Phe Ser Gly Val Pro Asp Arg Phe Thr Gly Ser
 65                  70                  75                  80

Gly Ser Gly Thr Asp Phe Thr Leu Thr Ile Ser Asn Val Gln Ser Glu
                 85                  90                  95

Asp Leu Ala Glu Tyr Phe Cys Gln Gln Tyr Asn Ser Tyr Pro Tyr Thr
                100                 105                 110

Phe Gly Gly Gly Thr Lys Leu Glu Ile Lys Arg Ala Asp Ala Ala Pro
            115                 120                 125

Thr Val Ser Ile Phe Pro Pro Ser Ser Glu Gln Leu Thr Ser Gly Gly
130                 135                 140

Ala Ser Val Val Cys Phe Leu Asn Asn Phe Tyr Pro Lys Asp Ile Asn
145                 150                 155                 160

Val Lys Trp Lys Ile Asp Gly Ser Glu Arg Gln Asn Gly Val Leu Asn
                165                 170                 175

Ser Trp Thr Asp Gln Asp Ser Lys Asp Ser Thr Tyr Ser Met Ser Ser
            180                 185                 190

Thr Leu Thr Leu Thr Lys Asp Glu Tyr Glu Arg His Asn Ser Tyr Thr
        195                 200                 205

Cys Glu Ala Thr His Lys Thr Ser Thr Ser Pro Ile Val Lys Ser Phe
210                 215                 220

Asn Arg Asn Glu Cys
225

<210> SEQ ID NO 41
<211> LENGTH: 107
<212> TYPE: PRT
<213> ORGANISM: Mus musculus

<400> SEQUENCE: 41

Asp Ile Val Met Thr Gln Ser Gln Lys Phe Met Ser Thr Ser Val Gly
 1               5                  10                  15

Asp Arg Val Ser Val Thr Cys Lys Ala Ser Gln Asn Val Gly Thr Asn
                20                  25                  30

Val Ala Trp Tyr Gln Gln Lys Pro Gly Gln Ser Pro Lys Ala Leu Ile
            35                  40                  45

Tyr Ser Ala Ser Tyr Arg Phe Ser Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Asn Ser Tyr Pro Tyr
                 85                  90                  95

Thr Phe Gly Gly Gly Thr Lys Leu Glu Ile Lys
                100                 105

<210> SEQ ID NO 42
<211> LENGTH: 11
<212> TYPE: PRT
<213> ORGANISM: Mus musculus

<400> SEQUENCE: 42

Lys Ala Ser Gln Asn Val Gly Thr Asn Val Ala
 1               5                  10
```

<210> SEQ ID NO 43
<211> LENGTH: 7
<212> TYPE: PRT
<213> ORGANISM: Mus musculus

<400> SEQUENCE: 43

```
Ser Ala Ser Tyr Arg Phe Ser
1               5
```

<210> SEQ ID NO 44
<211> LENGTH: 9
<212> TYPE: PRT
<213> ORGANISM: Mus musculus

<400> SEQUENCE: 44

```
Gln Gln Tyr Asn Ser Tyr Pro Tyr Thr
1               5
```

<210> SEQ ID NO 45
<211> LENGTH: 233
<212> TYPE: PRT
<213> ORGANISM: Mus musculus
<220> FEATURE:
<221> NAME/KEY: CHAIN
<222> LOCATION: (1)...(233)
<223> OTHER INFORMATION: AB0046 kappa light chain

<400> SEQUENCE: 45

```
Met Ser Ser Ala Gln Phe Leu Gly Leu Leu Leu Leu Cys Phe Gln Gly
1               5                   10                  15

Thr Arg Cys Asp Ile Gln Met Thr Gln Thr Thr Ser Ser Leu Ser Ala
            20                  25                  30

Ser Leu Gly Asp Arg Val Thr Ile Ser Cys Ser Ala Ser Gln Gly Ile
        35                  40                  45

Ser Asn Tyr Leu Asn Trp Tyr Gln Gln Lys Pro Asp Gly Thr Phe Lys
    50                  55                  60

Leu Leu Ile Tyr Tyr Thr Ser Ile Leu His Ser Gly Val Pro Ser Arg
65                  70                  75                  80

Phe Ser Gly Ser Gly Ser Gly Thr Asp Tyr Ser Leu Thr Ile Ser Asn
                85                  90                  95

Leu Glu Pro Glu Asp Ile Ala Thr Tyr Tyr Cys Gln Gln Tyr Gly Trp
            100                 105                 110

Leu Pro Arg Thr Phe Gly Gly Gly Thr Lys Leu Glu Ile Lys Arg Ala
        115                 120                 125

Asp Ala Ala Pro Thr Val Ser Ile Phe Pro Pro Ser Ser Glu Gln Leu
    130                 135                 140

Thr Ser Gly Gly Ala Ser Val Val Cys Phe Leu Asn Asn Phe Tyr Pro
145                 150                 155                 160

Lys Asp Ile Asn Val Lys Trp Lys Ile Asp Gly Ser Glu Arg Gln Asn
                165                 170                 175

Gly Val Leu Asn Ser Trp Thr Asp Gln Asp Ser Lys Asp Ser Thr Tyr
            180                 185                 190

Ser Met Ser Ser Thr Leu Thr Leu Thr Lys Asp Glu Tyr Glu Arg His
        195                 200                 205

Asn Ser Tyr Thr Cys Glu Ala Thr His Lys Thr Ser Thr Ser Pro Ile
    210                 215                 220

Val Lys Ser Phe Asn Arg Asn Glu Cys
225                 230
```

<210> SEQ ID NO 46
<211> LENGTH: 460
<212> TYPE: PRT
<213> ORGANISM: Mus musculus
<220> FEATURE:
<221> NAME/KEY: CHAIN
<222> LOCATION: (1)...(460)
<223> OTHER INFORMATION: AB0046 IgG1 heavy chain

<400> SEQUENCE: 46

```
Met Gly Trp Ser Ser Ile Ile Leu Phe Leu Val Ala Thr Ala Thr Gly
1               5                   10                  15

Val His Ser Gln Val Gln Leu Gln Gln Pro Gly Ser Val Leu Val Arg
            20                  25                  30

Pro Gly Ala Ser Val Lys Leu Ser Cys Thr Ala Ser Gly Tyr Thr Phe
        35                  40                  45

Thr Ser Tyr Trp Met Asn Trp Val Lys Gln Arg Pro Gly Gln Gly Leu
    50                  55                  60

Glu Trp Ile Gly Glu Ile Tyr Pro Ile Ser Gly Arg Thr Asn Tyr Asn
65                  70                  75                  80

Glu Lys Phe Lys Val Lys Ala Thr Leu Thr Val Asp Thr Ser Ser Ser
                85                  90                  95

Thr Ala Tyr Met Asp Leu Asn Ser Leu Thr Ser Glu Asp Ser Ala Val
            100                 105                 110

Tyr Tyr Cys Ala Arg Ser Arg Ala Asn Trp Asp Asp Tyr Trp Gly Gln
        115                 120                 125

Gly Thr Thr Leu Thr Val Ser Ser Ala Lys Thr Thr Pro Pro Ser Val
    130                 135                 140

Tyr Pro Leu Ala Pro Gly Ser Ala Ala Gln Thr Asn Ser Met Val Thr
145                 150                 155                 160

Leu Gly Cys Leu Val Lys Gly Tyr Phe Pro Glu Pro Val Thr Val Thr
                165                 170                 175

Trp Asn Ser Gly Ser Leu Ser Ser Gly Val His Thr Phe Pro Ala Val
            180                 185                 190

Leu Gln Ser Asp Leu Tyr Thr Leu Ser Ser Ser Val Thr Val Pro Ser
        195                 200                 205

Ser Thr Trp Pro Ser Glu Thr Val Thr Cys Asn Val Ala His Pro Ala
    210                 215                 220

Ser Ser Thr Lys Val Asp Lys Lys Ile Val Pro Arg Asp Cys Gly Cys
225                 230                 235                 240

Lys Pro Cys Ile Cys Thr Val Pro Glu Val Ser Ser Val Phe Ile Phe
                245                 250                 255

Pro Pro Lys Pro Lys Asp Val Leu Thr Ile Thr Leu Thr Pro Lys Val
            260                 265                 270

Thr Cys Val Val Val Asp Ile Ser Lys Asp Asp Pro Glu Val Gln Phe
        275                 280                 285

Ser Trp Phe Val Asp Asp Val Glu Val His Thr Ala Gln Thr Gln Pro
    290                 295                 300

Arg Glu Glu Gln Phe Asn Ser Thr Phe Arg Ser Val Ser Glu Leu Pro
305                 310                 315                 320

Ile Met His Gln Asp Trp Leu Asn Gly Lys Glu Phe Lys Cys Arg Val
                325                 330                 335

Asn Ser Ala Ala Phe Pro Ala Pro Ile Glu Lys Thr Ile Ser Lys Thr
            340                 345                 350
```

```
Lys Gly Arg Pro Lys Ala Pro Gln Val Tyr Thr Ile Pro Pro Lys
            355                 360                 365

Glu Gln Met Ala Lys Asp Lys Val Ser Leu Thr Cys Met Ile Thr Asp
370                 375                 380

Phe Phe Pro Glu Asp Ile Thr Val Glu Trp Gln Trp Asn Gly Gln Pro
385                 390                 395                 400

Ala Glu Asn Tyr Lys Asn Thr Gln Pro Ile Met Asp Thr Asp Gly Ser
                405                 410                 415

Tyr Phe Val Tyr Ser Lys Leu Asn Val Gln Lys Ser Asn Trp Glu Ala
                420                 425                 430

Gly Asn Thr Phe Thr Cys Ser Val Leu His Glu Gly Leu His Asn His
            435                 440                 445

His Thr Glu Lys Ser Leu Ser His Ser Pro Gly Lys
        450                 455                 460

<210> SEQ ID NO 47
<211> LENGTH: 117
<212> TYPE: PRT
<213> ORGANISM: Mus musculus

<400> SEQUENCE: 47

Gln Val Gln Leu Gln Gln Pro Gly Ser Val Leu Val Arg Pro Gly Ala
1               5                   10                  15

Ser Val Lys Leu Ser Cys Thr Ala Ser Gly Tyr Thr Phe Thr Ser Tyr
                20                  25                  30

Trp Met Asn Trp Val Lys Gln Arg Pro Gly Gln Gly Leu Glu Trp Ile
            35                  40                  45

Gly Glu Ile Tyr Pro Ile Ser Gly Arg Thr Asn Tyr Asn Glu Lys Phe
        50                  55                  60

Lys Val Lys Ala Thr Leu Thr Val Asp Thr Ser Ser Thr Ala Tyr
65                  70                  75                  80

Met Asp Leu Asn Ser Leu Thr Ser Glu Asp Ser Ala Val Tyr Tyr Cys
                85                  90                  95

Ala Arg Ser Arg Ala Asn Trp Asp Asp Tyr Trp Gly Gln Gly Thr Thr
            100                 105                 110

Leu Thr Val Ser Ser
        115

<210> SEQ ID NO 48
<211> LENGTH: 107
<212> TYPE: PRT
<213> ORGANISM: Mus musculus

<400> SEQUENCE: 48

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
                20                  25                  30

Leu Asn Trp Tyr Gln Gln Lys Pro Asp Gly Thr Phe Lys Leu Leu Ile
            35                  40                  45

Tyr Tyr Thr Ser Ile Leu His Ser Gly Val Pro Ser Arg Phe Ser Gly
        50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Gly Trp Leu Pro Arg
                85                  90                  95
```

```
Thr Phe Gly Gly Gly Thr Lys Leu Glu Ile Lys
            100                 105
```

<210> SEQ ID NO 49
<211> LENGTH: 461
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(461)
<223> OTHER INFORMATION: AB0045 heavy chain

<400> SEQUENCE: 49

```
Met Gly Trp Ser Leu Ile Leu Leu Phe Leu Val Ala Val Ala Thr Arg
1               5                   10                  15

Val His Ser Gln Val Gln Leu Gln Glu Ser Gly Pro Gly Leu Val Lys
            20                  25                  30

Pro Ser Glu Thr Leu Ser Leu Thr Cys Thr Val Ser Gly Phe Ser Leu
        35                  40                  45

Leu Ser Tyr Gly Val His Trp Val Arg Gln Pro Pro Gly Lys Gly Leu
    50                  55                  60

Glu Trp Leu Gly Val Ile Trp Thr Gly Gly Thr Thr Asn Tyr Asn Ser
65                  70                  75                  80

Ala Leu Met Ser Arg Phe Thr Ile Ser Lys Asp Asp Ser Lys Asn Thr
                85                  90                  95

Val Tyr Leu Lys Met Asn Ser Leu Lys Thr Glu Asp Thr Ala Ile Tyr
            100                 105                 110

Tyr Cys Ala Arg Tyr Tyr Tyr Gly Met Asp Tyr Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Cys Ser Arg Ser Thr Ser Glu Ser Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Lys Thr Tyr Thr Cys Asn Val Asp His Lys Pro Ser
    210                 215                 220

Asn Thr Lys Val Asp Lys Arg Val Glu Ser Lys Tyr Gly Pro Pro Cys
225                 230                 235                 240

Pro Pro Cys Pro Ala Pro Glu Phe Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser Gln Glu Asp Pro Glu Val Gln
        275                 280                 285

Phe Asn Trp Tyr Val Asp Gly Val Glu Val His Asn Ala Lys Thr Lys
    290                 295                 300

Pro Arg Glu Glu Gln Phe Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335
```

```
Val Ser Asn Lys Gly Leu Pro Ser Ser Ile Glu Lys Thr Ile Ser Lys
            340                 345                 350

Ala Lys Gly Gln Pro Arg Glu Pro Gln Val Tyr Thr Leu Pro Pro Ser
            355                 360                 365

Gln Glu Glu Met Thr Lys Asn Gln Val Ser Leu Thr Cys Leu Val Lys
        370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Arg Leu Thr Val Asp Lys Ser Arg Trp Gln
                420                 425                 430

Glu Gly Asn Val Phe Ser Cys Ser Val Met His Glu Ala Leu His Asn
            435                 440                 445

His Tyr Thr Gln Lys Ser Leu Ser Leu Ser Leu Gly Lys
        450                 455                 460

<210> SEQ ID NO 50
<211> LENGTH: 234
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)...(234)
<223> OTHER INFORMATION: AB0045 light chain

<400> SEQUENCE: 50

Met Arg Val Pro Ala Gln Leu Leu Gly Leu Leu Leu Leu Trp Leu Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Arg Asn Thr Val Ala Trp Tyr Gln Gln Lys Pro Gly Lys Ala Pro
    50                  55                  60

Lys Leu Leu Ile Tyr Ser Ser Tyr Arg Asn Thr Gly Val Pro Asp
65                  70                  75                  80

Arg Phe Ser Gly Ser Gly Ser Gly Thr Asp Phe Thr Leu Thr Ile Ser
                85                  90                  95

Ser Leu Gln Ala Glu Asp Val Ala Val Tyr Tyr Cys Gln Gln His Tyr
            100                 105                 110

Ile Thr Pro Tyr Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
```

Val Thr Lys Ser Phe Asn Arg Gly Glu Cys
225                 230

<210> SEQ ID NO 51
<211> LENGTH: 10
<212> TYPE: PRT
<213> ORGANISM: Mus musculus

<400> SEQUENCE: 51

Gly Tyr Thr Phe Thr Ser Tyr Trp Met Asn
1               5                   10

<210> SEQ ID NO 52
<211> LENGTH: 17
<212> TYPE: PRT
<213> ORGANISM: Mus musculus

<400> SEQUENCE: 52

Glu Ile Tyr Pro Ile Ser Gly Arg Thr Asn Tyr Asn Glu Lys Phe Lys
1               5                   10                  15
Val

<210> SEQ ID NO 53
<211> LENGTH: 8
<212> TYPE: PRT
<213> ORGANISM: Mus musculus

<400> SEQUENCE: 53

Ser Arg Ala Asn Trp Asp Asp Tyr
1               5

<210> SEQ ID NO 54
<211> LENGTH: 11
<212> TYPE: PRT
<213> ORGANISM: Mus musculus

<400> SEQUENCE: 54

Ser Ala Ser Gln Gly Ile Ser Asn Tyr Leu Asn
1               5                   10

<210> SEQ ID NO 55
<211> LENGTH: 7
<212> TYPE: PRT
<213> ORGANISM: Mus musculus

<400> SEQUENCE: 55

Tyr Thr Ser Ile Leu His Ser
1               5

<210> SEQ ID NO 56
<211> LENGTH: 9
<212> TYPE: PRT
<213> ORGANISM: Mus musculus

<400> SEQUENCE: 56

Gln Gln Tyr Gly Trp Leu Pro Arg Thr
1               5

<210> SEQ ID NO 57
<211> LENGTH: 441
<212> TYPE: PRT
<213> ORGANISM: Mus musculus

<400> SEQUENCE: 57

```
Gln Val Gln Leu Gln Gln Pro Gly Ser Val Leu Val Arg Pro Gly Ala
1               5                   10                  15

Ser Val Lys Leu Ser Cys Thr Ala Ser Gly Tyr Thr Phe Thr Ser Tyr
            20                  25                  30

Trp Met Asn Trp Val Lys Gln Arg Pro Gly Gln Gly Leu Glu Trp Ile
        35                  40                  45

Gly Glu Ile Tyr Pro Ile Ser Gly Arg Thr Asn Tyr Asn Glu Lys Phe
    50                  55                  60

Lys Val Lys Ala Thr Leu Thr Val Asp Thr Ser Ser Ser Thr Ala Tyr
65                  70                  75                  80

Met Asp Leu Asn Ser Leu Thr Ser Glu Asp Ser Ala Val Tyr Tyr Cys
                85                  90                  95

Ala Arg Ser Arg Ala Asn Trp Asp Asp Tyr Trp Gly Gln Gly Thr Thr
            100                 105                 110

Leu Thr Val Ser Ser Ala Lys Thr Thr Pro Pro Ser Val Tyr Pro Leu
        115                 120                 125

Ala Pro Gly Ser Ala Ala Gln Thr Asn Ser Met Val Thr Leu Gly Cys
    130                 135                 140

Leu Val Lys Gly Tyr Phe Pro Glu Pro Val Thr Val Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Pro Ser Ser Thr Trp
            180                 185                 190

Pro Ser Glu Thr Val Thr Cys Asn Val Ala His Pro Ala Ser Ser Thr
        195                 200                 205

Lys Val Asp Lys Ile Val Pro Arg Asp Cys Gly Cys Lys Pro Cys
210                 215                 220

Ile Cys Thr Val Pro Glu Val Ser Ser Val Phe Ile Phe Pro Pro Lys
225                 230                 235                 240

Pro Lys Asp Val Leu Thr Ile Thr Leu Thr Pro Lys Val Thr Cys Val
                245                 250                 255

Val Val Asp Ile Ser Lys Asp Asp Pro Glu Val Gln Phe Ser Trp Phe
            260                 265                 270

Val Asp Asp Val Glu Val His Thr Ala Gln Thr Gln Pro Arg Glu Glu
        275                 280                 285

Gln Phe Asn Ser Thr Phe Arg Ser Val Ser Glu Leu Pro Ile Met His
    290                 295                 300

Gln Asp Trp Leu Asn Gly Lys Glu Phe Lys Cys Arg Val Asn Ser Ala
305                 310                 315                 320

Ala Phe Pro Ala Pro Ile Glu Lys Thr Ile Ser Lys Thr Lys Gly Arg
                325                 330                 335

Pro Lys Ala Pro Gln Val Tyr Thr Ile Pro Pro Lys Glu Gln Met
            340                 345                 350

Ala Lys Asp Lys Val Ser Leu Thr Cys Met Ile Thr Asp Phe Phe Pro
        355                 360                 365

Glu Asp Ile Thr Val Glu Trp Gln Trp Asn Gly Gln Pro Ala Glu Asn
    370                 375                 380

Tyr Lys Asn Thr Gln Pro Ile Met Asp Thr Asp Gly Ser Tyr Phe Val
385                 390                 395                 400

Tyr Ser Lys Leu Asn Val Gln Lys Ser Asn Trp Glu Ala Gly Asn Thr
                405                 410                 415
```

```
Phe Thr Cys Ser Val Leu His Glu Gly Leu His Asn His His Thr Glu
            420                 425                 430

Lys Ser Leu Ser His Ser Pro Gly Lys
        435                 440

<210> SEQ ID NO 58
<211> LENGTH: 214
<212> TYPE: PRT
<213> ORGANISM: Mus musculus

<400> SEQUENCE: 58

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Phe Lys Leu Leu Ile
        35                  40                  45

Tyr Tyr Thr Ser Ile Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Gly Trp Leu Pro Arg
            85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
            165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
            195                 200                 205

Phe Asn Arg Asn Glu Cys
            210
```

ANTIBODIES TO MATRIX METALLOPROTEINASE 9

CROSS-REFERENCE TO RELATED APPLICATIONS

This application is a continuation application of U.S. application Ser. No. 16/245,169, filed Jan. 10, 2019, which is a continuation application of U.S. application Ser. No. 15/376,232, filed Dec. 12, 2016, which is a divisional application of U.S. application Ser. No. 14/382,301, filed Jan. 26, 2015, now U.S. Pat. No. 9,550,836, issued on Jan. 24, 2017, which is the National Stage filing of PCT/US2017/027160 with the International Filing Date of Feb. 29, 2012, all of which are hereby incorporated by reference in their entireties.

SUBMISSION OF SEQUENCE LISTING ON ASCII TEXT FILE 10001.11 The content of the following submission on ASCII text file is incorporated herein by reference in its entirety: a computer readable form (CRF) of the Sequence Listing (file name: 616082011103SEQLIST.TXT, date recorded: Aug. 26, 2020, size: 70 KB).

FIELD

This disclosure is in the field of extracellular enzymes, extracellular matrix enzymes, proteases and immunology.

BACKGROUND

Matrix metalloproteinases (MMPs) belong to a family of extracellular enzymes involved in forming and remodeling the extracellular matrix. These enzymes contain a conserved catalytic domain in which a zinc atom is coordinated by three histidine residues. Over members of this family are known, organized into a number of groups including collagenases, gelatinases, stromelysins, matrilysins, enamelysins and membrane MMPs.

MMP2 and MMP9 belong to the gelatinase group of matrix metalloproteinases. Besides containing signal peptide, propeptide, catalytic, zinc-binding and heamopexin-like domains common to most MMPs, the gelatinases also contain a plurality of fibronectin-like domains and an O-glycosylated domain.

MMPs are associated with a number of diseases. However, available inhibitors of MMPs have been unsuccessful, in part due to toxicity and lack of efficacy. Therefore, there is a need for specific and effective MMP inhibitors.

SUMMARY

The present disclosure provides compositions and methods of use involving binding proteins, e.g., antibodies and antigen-binding fragments thereof, that bind to matrix metalloproteinase-9 (MMP9) protein (also known as gelatinase-B). The binding proteins typically are antibodies or fragments (e.g., antigen-binding fragments) thereof and typically contain an immunoglobulin (Ig) heavy chain (or functional fragment thereof) and an Ig light chain (or functional fragment thereof). The heavy chain is typically an IgG, typically a human IgG, such as an IgG1 or IgG4, or other IgG such as an IgG2, or modified version thereof. The light chain typically is a kappa chain.

Among the MMP9 binding proteins, e.g., antibodies, are those that bind specifically to MMP9 and not to other matrix metalloproteinases. Such MMP9 binding proteins find use in applications in which it is necessary or desirable to obtain specific modulation (e.g., inhibition) of MMP9, e.g., without directly affecting the activity of other matrix metalloproteinases. Thus, in certain embodiments of the present disclosure an anti-MMP9 antibody or fragment thereof is a specific inhibitor of the activity of MMP9. In some aspects, the MMP9 binding proteins disclosed herein will be useful for inhibition of MMP9 while allowing normal function of other, related matrix metalloproteinases.

The antibodies and fragments can be described with reference to their amino acid sequences or portions thereof, and/or various functions such as binding specificity to MMP9 or particular epitopes thereof or the ability to compete for binding to epitopes on MMP9 with particular antibodies, and/or activity, such as the ability to inhibit MMP9, e.g., non-competitively.

The antibodies and fragments include those having a heavy chain variable (VH) region having a heavy chain complementary determining region (CDR) with an amino acid sequence of SEQ ID NO: 13, SEQ ID NO: 14, or SEQ ID NO: 15; those having a light chain variable (VL) region having a light chain complementary determining region (CDR) with an amino acid sequence of SEQ ID NO: 16, SEQ ID NO: 17, or SEQ ID NO: 18. Exemplary antibodies and fragments include those having a heavy chain CDR1 with the amino acid sequence of SEQ ID NO: 13, a heavy chain CDR2 with the amino acid sequence of SEQ ID NO: 14, and a heavy chain CDR3 with the amino acid sequence of SEQ ID NO: 15, and those having a heavy chain CDR3 of SEQ ID NO: 15. Exemplary antibodies and fragments further include those with a light chain CDR1 with the amino acid sequence of SEQ ID NO: 16, a light chain CDR2 with the amino acid sequence of SEQ ID NO: 17, and a light chain CDR3 with the amino acid sequence of SEQ ID NO: 18, and those having a light chain CDR3 with the amino acid sequence of SEQ ID NO: 18, as well as those having heavy chain CDRs of SEQ ID NOs: 13, 14, and 15, and light chain CDRs of SEQ ID NOs: 16, 17, and 18.

Exemplary antibodies and fragments further include those having a heavy chain CDR1 with the amino acid sequence of SEQ ID NO: 34, a heavy chain CDR2 with the amino acid sequence of SEQ ID NO: 35, and a heavy chain CDR3 with the amino acid sequence of SEQ ID NO: 36, those with a heavy chain CDR3 with the amino acid sequence of SEQ ID NO: 36, those with a light chain CDR1 with the amino acid sequence of SEQ ID NO: 37, a light chain CDR2 with the amino acid sequence of SEQ ID NO: 38, and a light chain CDR3 with the amino acid sequence of SEQ ID NO: 39, those with a light chain CDR3 with the amino acid sequence of SEQ ID NO: 39, as well as those having heavy chain CDRs of SEQ ID NOs: 34, 35, and 36, and light chain CDRs of SEQ ID NOs: 37, 38, and 39.

Exemplary antibodies and fragments further include those having a light chain CDR1 with the amino acid sequence of SEQ ID NO: 42, a light chain CDR2 with the amino acid sequence of SEQ ID NO: 43, and a light chain CDR3 with the amino acid sequence of SEQ ID NO: 44, and those with a light chain CDR3 with the amino acid sequence of SEQ ID NO: 44.

The antibodies and fragments further include those having a VH region with an amino acid sequence set forth in SEQ ID NO: 3, SEQ ID NO: 5, SEQ ID NO: 6, SEQ ID NO: 7, or SEQ ID NO: 8, and those having a VL region with an amino acid sequence set forth in SEQ ID NO: 4, SEQ ID NO: 9, SEQ ID NO: 10. SEQ ID NO: 11, or SEQ ID NO: 12, as well as antibodies and fragments having a VH region with an amino acid sequence set forth in SEQ ID NO: 3, SEQ ID NO: 5, SEQ ID NO: 6, SEQ ID NO: 7, or SEQ ID NO: 8 and a VL region with an amino acid sequence set forth in SEQ ID NO: 4, SEQ ID NO: 9, SEQ ID NO: 10, SEQ ID NO: 11, or SEQ ID NO: 12. In a particular example, the antibodies or fragments have a VH region of SEQ ID NO: 7 and a VL region of SEQ ID NO: 12, or at least at or about 75%, 80%, 85%, 90%, 91%, 92%, 93%, 94%, 95%, 96%, 97%, 98%, 99% or more sequence identity with such sequences. They further include those having a VI region with an amino acid sequence set forth in SEQ ID NO: 32 or 47, and those with a VL region with an amino acid sequence set forth in SEQ ID NO: 33 or in SEQ ID NO: 41 or in SEQ ID NO: 48, and combinations thereof, and sequence having at least at or about 75%, 80%, 85%, 90%, 91%, 92%, 93%, 94%, 95%, 96%, 97%, 98%, 99% or more sequence identity with such sequences.

The antibodies and fragments further include those having a VH region with an amino acid sequence set forth in SEQ ID NO: 1, and/or having a VL region with an amino acid sequence set forth in SEQ ID NO: 2, and/or a VH or VL region having at least at or about 75%, 80%, 85%, 90%, 91%, 92%, 93%, 94%, 95%, 96%, 97%, 98%, 99% or more sequence identity with such sequences.

In some cases, the heavy chain is encoded by a polynucleotide having a nucleotide sequence selected from the group consisting of SEQ ID NOs: 19-22 and the light chain is encoded by a polynucleotide having a nucleotide sequence selected from the group consisting of SEQ ID NOs: 23-26.

In some embodiments, the antibodies or fragments thereof inhibit the enzymatic activity of MMP9, such as by non-competitive inhibition.

The antibodies and fragments further include those that specifically bind to a given epitope of MMP9. In some cases, the epitope is an epitope specifically bound by any of the above-described antibodies. In one example, the epitope contains an amino acid residue (i.e., one or more amino acid residue(s)) outside of cysteine-switch active pocket of SEQ ID NO: 27. In certain examples, the epitope includes an amino acid residue (i.e., one or more amino acid residue(s)) within a given region of MMP9, for example, where the region is residues 104-202 of SEQ ID NO: 27. In some examples, the epitope includes an amino acid residue (i.e., one or more amino acid residue(s)) within a given region of MMP9, for example, where the region is residues 104-119, residues 159-166, or residues 191-202 of SEQ ID NO: 27. In one example, the epitope includes an amino acid residue (i.e., one or more amino acid residue) within a region of MMP9 that is residues 104-119 of SEQ ID NO: 27, an amino acid residue within a region of MMP9 that is residues 159-166 of SEQ ID NO: 27, and an amino acid residue within a region of MMP9 that is residues 191-202 of SEQ ID NO: 27. In some cases, the epitope includes E111, D113, R162, or I198 of SEQ ID NO: 27. In some cases, it includes R162 of SEQ ID NO: 27. In some cases, it includes E111, D113, R162, and I198 of SEQ ID NO: 27.

In some cases, the antibody or fragment is human or is humanized.

In some examples, the antibodies and fragments specifically bind to human MMP9 with a dissociation constant ($K_d$) equal to or lower than 100 nM, optionally lower than 10 nM, optionally lower than 1 nM, optionally lower than 0.5 nM, optionally lower than 0.1 nM, optionally lower than 0.01 nM, or optionally lower than 0.005 nM, in certain examples, between 0.1 and 0.2 nM, or between 0.1 and 10 µM, e.g., between 0.4 and 9 µm, such as between 0.4 and 8.8 µm, in the form of monoclonal antibody, scFv, Fab, or other form of antibody measured at a temperature of about 4° C. 25° C., 37° C. or 42° C.

Also among the provided antibodies and fragments are those having at least at or about 75%, 80%, 85%, 90%, 91%, 92%, 93%, 94%, 95%, 96%, 97%, 98%, 99% or more sequence identity with any of the above-described antibodies or containing various portions with at least at or about 75%, 80%, 85%, 90%, 91%, 92%, 93%, 94%, 95%, 96%, 97%, 98%, 99% or more sequence identity with the respective portions of the antibodies described above, such as having a VII region with such identity with SEQ ID NO: 7 and a VL region with such identity with SEQ ID NO: 12. Also provided are antibodies that compete for binding to MMP9 with any of the above-described antibodies, such as those that compete for binding to MMP9 with an antibody having a VH region with the amino acid sequence set forth in SEQ ID NO: 7 and a VL region with the amino acid sequence set forth in SEQ ID NO: 12.

Also provided are isolated nucleic acids encoding the antibodies and fragments, such as nucleic acids including a coding sequence for any of the above-described antibodies and fragments. Among the provided nucleic acids are those containing a nucleotide sequence encoding a heavy chain polypeptide comprising CDRs with the amino acid sequences set forth in SEQ ID NOs: 13-15, and/or a light chain polypeptide comprising CDRs with the amino acid sequences set forth in SEQ ID NOs: 16-18. In one example, the nucleotide sequence encodes the heavy chain polypeptide, which has an amino acid sequence selected from the group consisting of SEQ ID NOS: 1, 3, and 5-8. In another example, the nucleotide sequence encodes the light chain polypeptide, which has an amino acid sequence selected from the group consisting of SEQ ID NOS: 2, 4, and 9-12. In one example, the nucleotide sequence includes a sequence selected from the group consisting of SEQ ID NOs: 19-26, such as SEQ ID NO: 21, SEQ ID NO: 26, or SEQ ID NOs: 21 and 26. Also provided are vectors containing such nucleic acids and cells including the same, such as host cells.

Also provided are pharmaceutical compositions including the antibodies, fragments, nucleic acids, vectors, and cells. In some examples, the pharmaceutical compositions further include a carrier or excipient, such as a pharmaceutically acceptable or biologically acceptable carrier or excipient. In some cases, the pharmaceutical compositions are used in the provided therapeutic methods and uses.

Also provided are methods and uses of the antibodies, fragments, nucleic acids, vectors, cells, and compositions, for example in therapeutics, such as inhibiting MMP9 in a subject, and diagnostics, such as for detecting MMP9 in the subject.

For example, provided are diagnostic and prognostic methods involving detection of MMP9, and agents (such as any of the above-described anti-MMP9 antibodies and other MMP9 binding proteins) for use in such methods. In some cases, the diagnostic method detects MMP9 expression in a test sample from a subject. Such methods can be carried out, for example, by contacting the test sample with an antibody or fragment as described herein (such as any of the above-described antibodies or fragments) and detecting binding of the antibody or fragment to protein in the sample, thereby detecting the presence of MMP9. In some cases, a sample is first obtained or provided. In some examples, the methods include comparing the amount or level of MMP9 detected to a control level or amount, such as by comparing the amount of binding detected in the test sample with an amount of binding of the antibody or fragment to a control sample. In some cases, the methods involve simply comparing a test level and a control level of MMP9. In some cases, a higher test level (as compared to the control level) is indicative of the disease or condition.

In some cases, the MMP9 detected by the method indicates the presence of a disease or condition in the subject, such as an MMP9-associated disease or condition. In some cases, the methods further include treating the subject or adjusting (i.e., altering or discontinuing) treatment of the subject based on the results of the method, e.g., based on the levels of MMP9 detected in the sample. Among the biological samples are tissue, cells isolated from such tissues, and the like. In some cases, the methods are performed on liquid samples, such as blood, plasma, serum, whole blood, saliva, urine, or semen. Tissue samples include, for example, formalin-fixed or frozen tissue sections.

Also provided are methods of inhibiting MMP9 activity in a subject and/or treating a disease or condition in the subject, for example, using an agent that non-competitively inhibits MMP9, and agents (such as any of the above-described anti-MMP9 antibodies and other MMP9 binding proteins) for use in such methods. The methods generally are carried out by administering to the subject an MMP9 binding protein, such as an MMP9-binding antibody or fragment thereof as provided herein, e.g., in an effective amount. The antibody or fragment generally specifically binds to and non-competitively inhibits MMP9, for example, such that MMP9 activity is inhibited in the subject. In some cases, the antibody or fragment is one that binds MMP9 outside of the cysteine-switch active pocket, such as in one of the epitopes described above. In some cases, the antibody or fragment does not substantially bind to an MMP protein other than MMP9 and/or does not substantially bind to MMP2.

The subject generally is one with a disease or condition, typically one associated with increased or decreased MMP9 expression and/or activity. In certain cases, the subject with a disease or condition associated with increased MMP9 expression and/or activity. In other cases, the subject with a disease or condition associated with decreased MMP9 expression and/or activity.

Also provided are MMP9 polypeptides, including mutant MMP9 polypeptides, such as those containing residues 111-198 of SEQ ID NO: 27, and those having an amino acid sequence containing residues 111-198 of SEQ ID NO: 27 with an amino acid substitution at residue 111, 113, 162, or 198 of SEQ ID NO 27, or with an amino acid substitution at all such residues.

Also provided are uses of any of the above-described antibodies, nucleic acids, vectors, cells, and compositions, in the therapeutic and diagnostic methods described above.

BRIEF DESCRIPTION OF THE DRAWINGS

FIG. 1 shows the amino acid sequence of the heavy chain variable region of a mouse monoclonal anti-MMP9 antibody (AB0041), along with the amino acid sequences of humanized variants of heavy chain (VH1-VH4), aligned to show differences in framework amino acid sequence resulting from humanization. CDRs are shown in italics, and amino acids that are different in the humanized variants, compared to the parent mouse monoclonal, are underlined.

FIG. 2 shows the amino acid sequence of the light chain variable region of a mouse monoclonal anti-MMP9 antibody (AB0041), along with the amino acid sequences of humanized variants of this light chain (VH1-VH4), aligned to show differences in framework amino acid sequence resulting from humanization. CDRs are shown in italics, and amino acids that are different in the humanized variants, compared to the parent mouse monoclonal, are underlined.

FIG. 4 shows a comparison between the amino acid sequences of the heavy and light chains of antibodies designated AB0041, M4, and M12.

DETAILED DESCRIPTION

Figure 3:
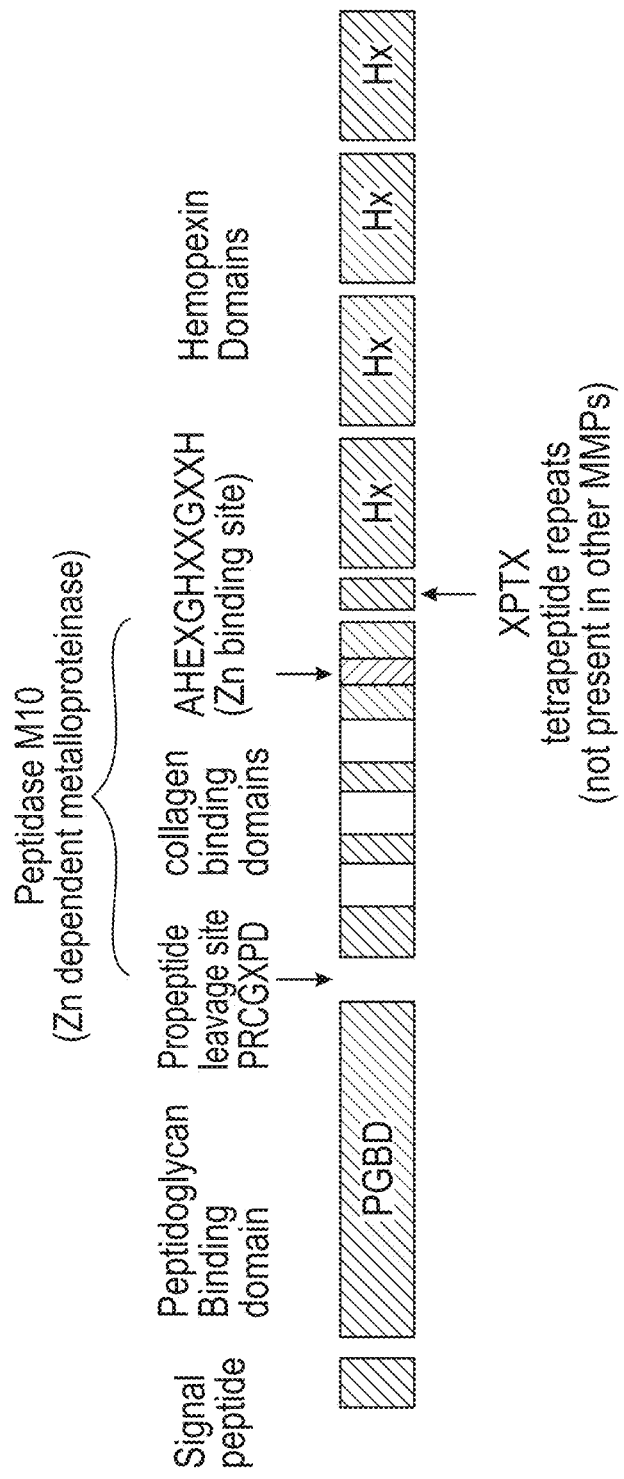
FIG. 3 shows a schematic diagram of the MMP9 protein.

Practice of the present disclosure employs, unless otherwise indicated, standard methods and conventional techniques in the fields of cell biology, toxicology, molecular biology, biochemistry, cell culture, immunology, oncology, recombinant DNA and related fields as are within the skill of the art. Such techniques are described in the literature and thereby available to those of skill in the art. See, for example, Alberts, B. et al., "Molecular Biology of the Cell," $5^{th}$ edition, Garland Science, New York, N.Y., 2008; Voet, D. et al. "Fundamentals of Biochemistry: Life at the Molecular Level," $3^{rd}$ edition, John Wiley & Sons, Hoboken, N.J., 2008; Sambrook, J. et al., "Molecular Cloning: A Laboratory Manual," 3 edition. Cold Spring Harbor Laboratory Press, 2001; Ausubel, F. et al., "Current Protocols in Molecular Biology." John Wiley & Sons, New York, 1987 and periodic updates; Freshney, R. I., "Culture of Animal Cells: A Manual of Basic Technique," $4^{th}$ edition, John Wiley & Sons, Somerset, N J, 2000; and the series "Methods in Enzymology," Academic Press, San Diego, Calif. See also, for example, "Current Protocols in Immunology," (R. Coico, series editor), Wiley, last updated August 2010.

Certain MMPs play roles in tumor growth, metastasis, inflammation, autoimmunity, and vascular disease. See, for example, Hu et al. (2007) *Nature Reviews: Drug Discovery* 6:480-498. Thus, it is desirable to inhibit the activity of one or more particular MMPs in certain therapeutic settings. While sharing significant homology at a sequence level, the expression and functional roles of the two gelatinases MMP9 and MMP2 vary significantly. MMP9 expression is induced by a number of disease associated cytokines and growth factors. Also, the MMP9 knockout mouse is protected in a variety of disease models, whereas MMP2 is more constitutively expressed and the MMP2 knockout animals tend toward little protection. Some studies have shown that MMP2 knockout mouse exhibited worse disease in challenge models. For some diseases or disorders, the activity of more than one MMPs is inhibited. In clinical studies, the inhibitors to more than one MMPs have caused adverse effects, such as toxicity or lack of efficacy, that are not desired. It has been shown that the activity of certain MMPs, e.g., MMP2, is often required for normal tissue homeostasis and/or is protective against disease. Certain available MMP inhibitors have caused side effects.

Among the provided embodiments are agents, including therapeutic reagents, such as antibodies and antigen-binding fragments thereof, that specifically inhibit the catalytic activity of a single MMP or a select plurality of MMPs, such as MMP9 and that do not react with or inhibit certain other MMPs or any other MMPs. Also among the provided embodiments are methods and uses of the same for treatment of various diseases.

MMP9 Binding Proteins

The present disclosure provides binding proteins, e.g., antibodies and fragments (e.g., antigen-binding fragments) thereof, that bind to the matrix metalloproteinase-9 (MMP9) protein (MMP9 is also known as gelatinase-B), e.g., human MMP9, such as the human MMP9 having an amino acid sequence set forth in SEQ ID NO: 27 or SEQ ID NO: 28. The binding proteins of the present disclosure generally comprise an immunoglobulin (Ig) heavy chain (or functional fragment thereof) and an Ig light chain (or functional fragment thereof).

The disclosure further provides MMP9 binding proteins that bind specifically to MMP9 and not to other matrix metalloproteinases such as MMP1, MMP2, MMP3, MMP7, MMP9, MMP10, MMP12, and MMP13. Such specific MMP9 binding proteins are thus generally not significantly or detectably crossreactive with non-MMP9 matrix metalloproteinases. MMP9 binding proteins that specifically bind MMP9 find use in applications in which it is necessary or desirable to obtain specific modulation (e.g., inhibition) of MMP9, e.g., without directly affecting the activity of other matrix metalloproteinases.

In certain embodiments of the present disclosure, an anti-MMP9 antibody is an inhibitor of the activity of MMP9, and can be a specific inhibitor of MMP9. In one embodiment, the MMP9 binding proteins disclosed herein is useful for inhibition of MMP9 while not affecting other matrix metalloproteinases. "An inhibitor of MMP" or "inhibitor of MMP9 activity" can be an antibody or an antigen binding fragment thereof that directly or indirectly inhibits activity of MMP9, including but not limited to enzymatic processing, inhibiting action of MMP9 on it substrate (e.g., by inhibiting substrate binding, substrate cleavage, and the like), and the like.

The present disclosure also provides MMP9 binding proteins that specifically bind to non-mouse MMP9, such as human MMP9, Cynomolgus monkey MMP9, and rat MMP9.

The present disclosure also provides MMP9 binding proteins (e.g., anti-MMP9 antibodies and functional fragments thereof) that act as non-competitive inhibitors. A "non-competitive inhibitor" refers to an inhibitor binds at site away from substrate binding site of an enzyme, and thus can bind the enzyme and effect inhibitory activity regardless of whether or not the enzyme is bound to its substrate. The non-competitive or allosteric inhibition is generally independent of substrate association or concentration. Such non-competitive inhibitors can, for example, provide for a level of inhibition that can be substantially independent of substrate concentration.

MMP9 binding proteins (e.g., antibodies and functional fragments thereof) of the present disclosure include those that bind MMP9, particularly human MMP9, and having a heavy chain polypeptide (or functional fragment thereof) that has at least about 80%, 85%, 90%, 95% or more amino acid sequence identity to a heavy chain polypeptide disclosed herein.

MMP9 binding proteins (e.g., antibodies and functional fragments thereof) of the present disclosure include those that bind MMP9, particularly human MMP9, and having a light polypeptide (or functional fragment thereof) that has at least about 80%, 85%, 90%, 95% or more amino acid sequence identity to a heavy chain polypeptide disclosed herein.

MMP9 binding proteins (e.g., antibodies and functional fragments thereof) of the present disclosure include those that hind MMP9, particularly human MMP9, and have a heavy chain polypeptide (or functional fragment thereof) having the complementarity determining regions ("CDRs") of heavy chain polypeptide and the CDRs of a light chain polypeptide (or functional fragment thereof) as disclosed herein.

"Homology" or "identity" or "similarity" as used herein in the context of nucleic acids and polypeptides refers to the relationship between two polypeptides or two nucleic acid molecules based on an alignment of the amino acid sequences or nucleic acid sequences, respectively. Homology and identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. In comparing two sequences, the absence of residues (amino acids or nucleic acids) or presence of extra residues also decreases the identity and homology/similarity.

As used herein, "identity" means the percentage of identical nucleotide or amino acid residues at corresponding positions in two or more sequences when the sequences are aligned to maximize sequence matching, i.e., taking into account gaps and insertions. Sequences are generally aligned for maximum correspondence over a designated region, e.g., a region at least about 20, 25, 30, 35, 40, 45, 50, 55, 60, 65 or more amino acids or nucleotides in length, and can be up to the full-length of the reference amino acid or nucleotide. For sequence comparison, typically one sequence acts as a reference sequence, to which test sequences are compared. When using a sequence comparison algorithm, test and reference sequences are input into a computer program, subsequence coordinates are designated, if necessary, and sequence algorithm program parameters are designated. The sequence comparison algorithm then calculates the percent sequence identity for the test sequence(s) relative to the reference sequence, based on the designated program parameters.

Examples of algorithms that are suitable for determining percent sequence identity are the BLAST and BLAST 2.0 algorithms, which are described in Altschul et al. (1990) J. Mol. Biol. 215: 403-410 and Altschul et al. (1977) Nucleic Acids Res. 25: 3389-3402, respectively. Software for performing BLAST analyses is publicly available through the National Center for Biotechnology Information (www.ncbi.nlmi.nih.gov). Further exemplary algorithms include ClustalW (Higgins D., et al. (1994) Nucleic Acids Res 22: 4673-4680), available at www.cbi.ac.uk/Tools/clustalw/index.html.

Residue positions which are not identical can differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine.

Sequence identity between two nucleic acids can also be described in terms of hybridization of two molecules to each other under stringent conditions. The hybridization conditions are selected following standard methods in the art (see, for example, Sambrook, et al., Molecular Cloning: A Laboratory Manual, Second Edition, (1989) Cold Spring Harbor. N.Y.). An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH7.6), 5×Denhardt's solution, 10% dextran sulfate, and 20 mg/ml denatured, sheared salmon sperm DNA, followed by washing the filters in 0.1×SSC at about 65° C. Stringent hybridization conditions are hybridization conditions that are at least as stringent as the above representative conditions, where conditions are considered to be at least as stringent if they are at least about 80% as stringent, typically at least 90% as stringent as the above specific stringent conditions.

Accordingly, the present disclosure provides, for example, antibodies or antigen binding fragments thereof, comprising a heavy chain variable region polypeptide having at least 80%, 85%, 90%, 95%, or greater amino acid sequence identity to an amino acid sequence of a heavy chain variable region described herein (e.g., SEQ ID NOS:1 or 5-8), and a variable light chain polypeptide having at least 80%, 85%, 90%, 95%, or greater amino acid sequence identity to an amino acid sequence of a light chain polypeptide as set forth herein (e.g., SEQ ID NOS:2 or 9-12).

Examples of anti-MMP9 antibodies of the present disclosure are described in more detail below.

Antibodies

The MMP9 binding proteins include antibodies and functional fragments thereof, such as those that specifically bind to MMP9. As used herein, the term "antibody" means an isolated or recombinant polypeptide binding agent that comprises peptide sequences (e.g., variable region sequences) that specifically bind an antigenic epitope. The term is used in its broadest sense and specifically covers monoclonal antibodies (including full-length monoclonal antibodies), polyclonal antibodies, human antibodies, humanized antibodies, chimeric antibodies, nanobodies, diabodies, multispecific antibodies (e.g., bispecific antibodies), and antibody fragments including but not limited to Fv, scFv, Fab, Fab'F(ab')$_2$ and Fab$_2$, so long as they exhibit the desired biological activity. The term "human antibody" refers to antibodies containing sequences of human origin, except for possible non-human CDR regions, and does not imply that the full structure of an immunoglobulin molecule be present, only that the antibody has minimal immunogenic effect in a human (i.e., does not induce the production of antibodies to itself).

An "antibody fragment" comprises a portion of a full-length antibody, for example, the antigen binding or variable region of a full-length antibody. Such antibody fragments may also be referred to herein as "functional fragments: or "antigen-binding fragments". Examples of antibody fragments include Fab, Fab', F(ab')$_2$, and Fv fragments; diabodies; linear antibodies (Zapata et al. (1995) *Protein Eng.* 8(10):1057-1062); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Fv" is a minimum antibody fragment containing a complete antigen-recognition and -binding site. This region consists of a dimer of one heavy- and one light-chain variable domain in tight, non-covalent association. It is in this configuration that the three complementarity-determining regions (CDRs) of each variable domain interact to define an antigen-binding site on the surface of the $V_H$-$V_L$ dimer. Collectively, the six CDRs confer antigen-binding specificity to the antibody. However, even a single variable domain (or an isolated $V_H$ or $V_L$ region comprising only three of the six CDRs specific for an antigen) has the ability to recognize and bind antigen, although generally at a lower affinity than does the entire F fragment.

The "$F_{ab}$" fragment also contains, in addition to heavy and light chain variable regions, the constant domain of the light chain and the first constant domain (CHI) of the heavy chain. Fab fragments were originally observed following papain digestion of an antibody. Fab' fragments differ from Fab fragments in that F(ab') fragments contain several additional residues at the carboxy terminus of the heavy chain CH$_1$ domain, including one or more cysteines from the antibody hinge region. F(ab')$_2$ fragments contain two Fab fragments joined, near the hinge region, by disulfide bonds, and were originally observed following pepsin digestion of an antibody. Fab'-SH is the designation herein for Fab' fragments in which the cysteine residue(s) of the constant domains bear a free thiol group. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to five major classes: IgA, IgD, IgE, IgG, and IgM, and several of these may be further divided into subclasses (isotypes), e.g., IgG1, IgG2, IgG3, IgG4, IgA1, and IgA2.

"Single-chain Fv" or "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see Pluckthun, in *The Pharmacology of Monoclonal Antibodies*, vol. 113 (Rosenburg and Moore eds.) Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain, thereby creating two antigen-binding sites. Diabodies are additionally described, for example, in EP 404,097; WO 93/11161 and Hollinger et al. (993) *Proc. Natl. Acad. Sci. USA* 90:6444-6448.

An "isolated" antibody is one that has been identified and separated and/or recovered from a component of its natural environment. Components of its natural environment may include enzymes, hormones, and other proteinaceous or nonproteinaceous solutes. In some embodiments, an isolated antibody is purified (1) to greater than 95% by weight of antibody as determined by the Lowry method, for example, more than 99% by weight, (2) to a degree sufficient to obtain at least 15 residues of N-terminal or internal amino acid sequence, e.g., by use of a spinning cup sequenator, or (3) to homogeneity by gel electrophoresis (e.g., SDS-PAGE) under reducing or nonreducing conditions, with detection by Coomassie blue or silver stain. The term "isolated antibody" includes an antibody in situ within recombinant cells, since at least one component of the antibody's natural environment will not be present. In certain embodiments, isolated antibody is prepared by at least one purification step.

As used herein, "immunoreactive" refers to antibodies or fragments thereof that are specific to a sequence of amino acid residues ("binding site" or "epitope"), yet if are cross-reactive to other peptides/proteins, are not toxic at the levels at which they are formulated for administration to human use. "Epitope" refers to that portion of an antigen capable of forming a binding interaction with an antibody or antigen binding fragment thereof. An epitope can be a linear peptide sequence (i.e., "continuous") or can be composed of non-contiguous amino acid sequences (i.e., "conformational" or "discontinuous"). The term "preferentially binds" means that the binding agent binds to the binding site with greater affinity than it binds unrelated amino acid sequences.

Anti-MMP9 antibodies can be described in terms of the CDRs of the heavy and light chains. As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

CDR Definitions

|  | Kabat[1] | Chothia[2] | MacCallum[3] |
| --- | --- | --- | --- |
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs.

In some embodiments, an antibody is a humanized antibody or a human antibody. Humanized antibodies include human immununoglobulins (recipient antibody) in which residues from a complementary-determining region (CDR) of the recipient are replaced by residues from a CDR of a non-human species (donor antibody) such as mouse, rat or rabbit having the desired specificity, affinity and capacity. Thus, humanized forms of non-human (e.g., murine) antibodies are chimeric immunoglobulins which contain minimal sequence derived from non-human immunoglobulin. The non-human sequences are located primarily in the variable regions, particularly in the complementarity-determining regions (CDRs). In some embodiments, Fv framework residues of the human immunoglobulin are replaced by corresponding non-human residues. Humanized antibodies can also comprise residues that are found neither in the recipient antibody nor in the imported CDR or framework sequences. In certain embodiments, a humanized antibody comprises substantially all of at least one, and typically two, variable domains, in which all or substantially all of the CDRs correspond to those of a non-human immunoglobulin and all or substantially all of the framework regions are those of a human immunoglobulin consensus sequence. For the purposes of the present disclosure, humanized antibodies can also include immunoglobulin fragments, such as Fv, Fab, Fab', F(ab')$_2$ or other antigen-binding subsequences of antibodies.

The humanized antibody can also comprise at least a portion of an immunoglobulin constant region (Fc), typically that of a human immunoglobulin. See, for example, Jones et al. (1986) Nature 321:522-525; Riechmann et al. (1988) Nature 332:323-329; and Presta (1992) Curr. Op. Struct. Biol. 2:593-596.

Methods for humanizing non-human antibodies are known in the art. Generally, a humanized antibody has on or more amino acid residues introduced into it from a source that is non-human. These non-human amino acid residues are often referred to as "import" or "donor" residues, which are typically obtained from an "import" or "donor" variable domain. For example, humanization can be performed essentially according to the method of Winter and co-workers, by substituting rodent CDRs or CDR sequences for the corresponding sequences of a human antibody. See, for example, Jones et al., supra; Riechmann et al., supra and Verhoeyen et al. (1988) Science 239:1534-1536. Accordingly, such "humanized" antibodies include chimeric antibodies (U.S. Pat. No. 4,816,567), wherein substantially less than an intact human variable domain has been substituted by the corresponding sequence from a non-human species. In certain embodiments, humanized antibodies are human antibodies in which some CDR residues and optionally some framework region residues are substituted by residues from analogous sites in rodent antibodies (e.g., murine monoclonal antibodies).

Human antibodies can also be produced, for example, by using phage display libraries. Hoogenboom et al. (1991) J. Mol. Biol, 227:381; Marks et al. (1991) J. Mol. Biol. 222:581. Other methods for preparing human monoclonal antibodies are described by Cole et al. (1985) "Monoclonal Antibodies and Cancer Therapy," Alan R. Liss, p. 77 and Boemer et al. (1991) J. Immunol. 147:86-95.

Human antibodies can be made by introducing human immunoglobulin loci into transgenic animals (e.g., mice) in which the endogenous immunoglobulin genes have been partially or completely inactivated. Upon immunological challenge, human antibody production is observed, which closely resembles that seen in humans in all respects, including gene rearrangement, assembly, and antibody repertoire. This approach is described, for example, in U.S. Pat.

Nos. 5,545,807; 5,545,806; 5,569,825; 5,625,126; 5,633,425; 5,661,016, and in the following scientific publications: Marks et al. (1992) *Bio/Technology* 10:779-783 (1992); Lonberg et al. (1994) *Nature* 368: 856-859; Morrison (1994) *Nature* 368:812-813; Fishwald et al. (1996) *Nature Biotechnology* 14:845-851; Neuberger (1996) *Nature Biotechnology* 14:826; and Lonberg et al. (1995) *Intern. Rev. Immunol.* 13:65-93.

Antibodies can be affinity matured using known selection and/or mutagenesis methods as described above. In some embodiments, affinity matured antibodies have an affinity which is five times or more, ten times or more, twenty times or more, or thirty times or more than that of the starting antibody (generally murine, rabbit, chicken, humanized or human) from which the matured antibody is prepared.

An antibody can also be a bispecific antibody. Bispecific antibodies are monoclonal, and may be human or humanized antibodies that have binding specificities for at least two different antigens. In the present case, the two different binding specificities can be directed to two different MMPs, or to two different epitopes on a single MMP (e.g., MMP9).

An antibody as disclosed herein can also be an immunoconjugate. Such immunoconjugates comprise an antibody (e.g., to MMP9) conjugated to a second molecule, such as a reporter An immunoconjugate can also comprise an antibody conjugated to a cytotoxic agent such as a chemotherapeutic agent, a toxin (e.g., an enzymatically active toxin of bacterial, fungal, plant, or animal origin, or fragments thereof), or a radioactive isotope (i.e., a radioconjugate).

An antibody that "specifically binds to" or is "specific for" a particular polypeptide or an epitope refers to the selective binding of the antibody to the target antigen or epitope; these terms, and methods for determining specific binding, are well understood in the art. An antibody exhibits "specific binding" for a particular target antigen or epitope if it binds with greater affinity, avidity, more readily, and/or with greater duration to that target antigen or epitope than it does with other substances. In some embodiments, the antibody that specifically binds to the polypeptide or epitope is one that that binds to that particular polypeptide or epitope without substantially binding to any other polypeptide or polypeptide epitope.

In some embodiments, the provided antibodies specifically bind to human MMP9 with a dissociation constant ($K_d$) equal to or lower than 10 nM, optionally lower than 10 nM, optionally lower than 1 nM, optionally lower than 0.5 nM, optionally lower than 0.1 nM, optionally lower than 0.01 nM, or optionally lower than 0.005 nM, in certain examples, between 0.1 and 0.2 nM, or between 0.1 and 10 pM, e.g., between 0.4 and 9 μm, such as between 0.4 and 8.8 μm, in the form of monoclonal antibody, scFv, Fab, or other form of antibody measured at a temperature of about 4° C., 25° C., 37° C. or 42° C.

In certain embodiments, an antibody of the present disclosure binds to one or more processing sites (e.g., sites of proteolytic cleavage) in MMP9, thereby effectively blocking processing of the proenzyme or preproenzyme to the catalytically active enzyme, and thus reducing the proteolytic activity of the MMP9.

In certain embodiments, an antibody according to the present disclosure binds to MMP9 with an affinity at least 2 times, at least 5 times, at least 10 times, at least 25 times, at least 50 times, at least 100 times, at least 500 times, or at least 1000 times greater than its binding affinity for another MMP. Binding affinity can be measured by any method known in the art and can be expressed as, for example, on-rate, off-rate, dissociation constant ($K_d$), equilibrium constant ($K_{eq}$) or any term in the art.

In certain embodiments, an antibody according to the present disclosure is one that inhibits the enzymatic (i.e., catalytic) activity of MMP9, such as a non-competitive inhibitor of the catalytic activity of MMP9. In certain embodiments, an antibody according to the present disclosure binds within the catalytic domain of MMP9. In additional embodiments, an antibody according to the present disclosure binds outside the catalytic domain of MMP9.

Also provided are antibodies or antigen binding fragments thereof that compete with any one or more of the anti-MMP9 antibodies or antigen binding fragments thereof described herein for binding to MMP9. Thus, the present disclosure contemplates anti-MMP9 antibodies, and functional fragments thereof, that compete for binding with, for example, an antibody having a heavy chain polypeptide of any of SEQ ID NOS: 1 or 5-8, a light chain polypeptide of SEQ ID NOS: 2 or 9-12, or combinations thereof. In one embodiment, the anti-MMP9 antibody, or functional fragment thereof, competes for binding to human MMP9 with the antibody described herein as AB0041.

Epitope Binding

Also provided are antibodies and fragments thereof that bind to the same epitope, e.g., MMP9 epitope as any one or more of the antibodies described herein. Also provided are antibodies and fragments that specifically bind to an epitope of MMP9, where the epitope includes an amino acid residue within a particular region of MMP9 or multiple regions of MMP9. Such regions can include, for example, structural loops and/or other structural domains of MMP9, such as those shown to be important for binding to exemplary antibodies described herein. Typically, the regions are defined according to amino acid residue positions on the full-length MMP9 sequence, e.g., SEQ ID NO: 27. In some examples, the epitope is outside of cysteine-switch active pocket of SEQ ID NO: 27. In some example, the epitope contains an amino acid residue (i.e., one or more amino acid residue(s)) within a region that is residues 104-202 of SEQ ID NO: 27. In one example, the epitope contains an amino acid residue (i.e., one or more amino acid residue(s)) within a region that is residues 104-119, residues 159-166, or residues 191-202 of SEQ ID NO: 27. In some aspects, the epitope includes an amino acid residue (i.e., one or more amino acid residue(s)) within a region of MMP9 that is residues 104-119 of SEQ ID NO: 27, an amino acid residue within a region of MMP9 that is residues 159-166 of SEQ ID NO: 27, and an amino acid residue within a region of MMP9 that is residues 191-202 of SEQ ID NO: 27. In some cases, the epitope includes E111, D113, R162, or I198 of SEQ ID NO: 27. In some cases, it includes R162 of SEQ ID NO: 27. In some cases, it includes E111, D113, R162, and I198 of SEQ ID NO: 27.

MMP9 Sequence

The amino acid sequence of human MMP9 protein is as follows:

(SEQ ID NO: 27)

```
MSLWQPLVLV LLVLGCCFAA PPQRQSTLVL FPGDLRTNLT DRQLAEEYLY  50

RYGYTRVAEM RGESKSLGPA LLLLQKQLSL PETGELDSAT LKAMRTPRCG 100

VPDLGRFQTF EGDLKWHHHN ITYWIQNYSE DLPRAVIDDA FARAFALWSA 150
```

```
                                                              -continued
VTPLTFTRVY SRDADIVIQF GVAEHGDGYP FDGKDGLLAH AFFPGPGIQG    200

DAHFDDDELW SLGKGVVVPT RFGNADGAAC HFPFIFEGRS YSACTTDGRS    250

DGLPWCSTTA NYDTDDRFGF CPSERLYTRD GNADGKPCQF PFIFQGQSYS    300

ACTTDGRSDG YRWCATTANY DRDKLFGFCP TRADSTVMGG NSAGELCVFP    350

FTFLGKEYST CTSEGRGDGP LWCATTSNFD SDKKWGFCPD QGYSLFLVAA    400

HEFGHALGLD HSSVPEALMY PMYRFTEGPP LHKDDVNGIR HLYGPRPEPE    450

PRPPITTTPQ PTAPPTVCPT GPPTVHPSER PTAGPTGPPS AGPTGPPTAG    500

PSTATTVPLS PVDDACNVNI FDATAEIGNQ LYLFKDGKYW RFSEGRGSRP    550

QGPFLIADKW PALPRKLDSV FEEPLSKKLF FFSGRQVWVY TGASVLGPRR    600

LDKLGLGADV AQVTGALRSG RGKMLLFSGR RLWRFDVKAQ MVDPRSASEV    650

DRMFPGVPLD THDVFQYREK AYFCQDRFYW RVSSRSELNQ VDQVGYVTYD    700

ILQCPED
```

Protein domains are shown schematically in FIG. 3 and are indicated below:

| Amino Acid # | Feature |
| --- | --- |
| 1-19 | Signal Peptide |
| 38-98 | Peptidoglycan Binding Domain |
| R98/C99 | Cysteine-switch active pocket |
| 112-445 | Zn dependent metalloproteinase domain |
| 223-271 | Fibronectin type II domain (gelatin binding domain) |
| 281-329 | Fibronectin type II domain (gelatin binding domain) |
| 340-388 | Fibronectin type II domain (gelatin binding domain) |
| 400-411 | Zn binding region |
| 521-565 | Hemopexin-like domain |
| 567-608 | Hemopexin-like domain |
| 613-659 | Hemopexin-like domain |
| 661-704 | Hemopexin-like domain |

The amino acid sequence of mature full-length human MMP9 (which is the amino acid sequence of the propolypeptide of SEQ ID NO:27 without the signal peptide) is:

```
                                             (SEQ ID NO: 28)
APRQRQSTLVL FPGDLRTNLT DRQLAEEYLY RYGYTRVAEM

RGESKSLGPA ILLLQKQLSL PETGELDSAT LKAMRTPRCG

VPDLGREQTE EGDLKWHHHN ITYWIQNYSE DLPRAVIDDA

FARAFALWSA VTPLTFTRVY SRDADIVIQF GVAEHGDGYP

FDGKDGLLAH AFPPGPGIQG DAEFDDDELW SLGEGVVVPT

RFGNADaAAC HFPFIFEGRS YSACTTDGRS DGLPWCSTTA

NYDTDDRFGF CPSERLYTPD GNADGKPCQF PFIFQGQSYS

ACTTDGRSDG YRWCATTANY DRDKLFGFCP TRADSTVMGG

NSAGELCVFP FTFLGKEYST CTSEGRGDGR LWCATTSNFD

SDKKWGFCPD QGYSLFLVAA HEFGHALGLD HSSVPEALMY

PMYRFTEGPP LHKDDVNGIR HLYGPRPEPE PRPPTTTTPQ

PTAPPTVCPT GPPTVHPSER PTAGPTGPPS AGPTGPPTAG

PSTATTVPLS PVDDACNVNI FDAIAEIGNQ LYLFKDGKYW

RFSEGRGSRP QGPFLIADKW PALPRKLDSV FEEPLSKKLF
```

```
                        -continued
FFSGRQVWVY TGASVLGPRR LDKLGLGADV AQVTGALRSG

RGKMLLFSGR RLWRFDVKAQ MVDPRSASEV DRMFPGVPLD

THDVFQYREK AYECQDREYW RVSSRSELNQ VDQVGYVTYD

ILQCPED
```

The amino acid sequence of the signal peptide is MSLWQPLVLV LLVLGCCFA (SEQ ID NO:29).

Also provided are MMP9 polypeptides, including mutant MMP9 polypeptides. Such peptides are useful, for example, in generating and selecting antibodies and fragments as provided herein. Exemplary polypeptides include those having an amino acid sequence containing residues 104-202 of SEQ ID NO: 27, and those having an amino acid sequence of SEQ ID NO: 27 with an amino acid substitution at residue 111, 113, 162, or 198 of SEQ ID NO 27 or with an amino acid substitution at all such residues. Other exemplary polypeptides include those having an amino acid sequence containing residues 111-198 of SEQ ID NO: 27, and those having an amino acid sequence containing residues 111-198 of SEQ ID NO: 27 with an amino acid substitution at residue 111, 113, 162, or 198 of SEQ ID NO 27 or with an amino acid substitution at all such residues. Such polypeptides find use, for example, in selecting antibodies that bind to epitopes containing such residues and/or for which such residues of MMP9 are important for binding, such as those described herein.

The present disclosure contemplates MMP9 binding proteins that bind any portion of MMP9, e.g., human MMP9, with MMP9 binding proteins that preferentially bind MMP9 relative to other MMPs being of particular interest.

Anti-MMP9 antibodies, and functional fragments thereof, can be generated accordingly to methods well known in the art. Exemplary anti-MMP9 antibodies are provided below.

Mouse Monoclonal Anti-MMP9 Antibodies

A mouse monoclonal antibody to human MMP9 was obtained as described in Example 1. This antibody contains a mouse IgG2b heavy chain and a mouse kappa light chain, and is denoted AB0041.

The amino acid sequence of the AB0041 heavy chain is as follows:

```
                                        (SEQ ID NO: 1)
MAVLVLFLCLVAFPSCVLSQVQLKESGPGLVAPSQSLSITC

TVSGFSLLSYGVHWVRQPPGKGLEWLGVIWTGGTTNYNSAL

MSRLSISKDDSKSQVFLKMNSLQTDDTAIYYCARYYYGMDY

WGQGTSVTVSSAKTTPPSVYPLAPGCGDTTGSSVTLGCLVK

GYFPESVTVTWNSGSLSSSVHTFPALLQSGLYTMSSSVTVP

SSTWPSQTVTCSVAHPASSTTVDKKLEPSGPISTINPCPPC

KECHKCPAPNLEGGPSVFIFPPNIKDVLMISLTPKVTCVVV

DVSEDDPDVRISWFVNNVEVHTAQTQTHREDYNSTIRVVSA

LPIQHQDWMSGKEFKCKVNNKDLPSPIERTISKIKGLVRAP

QVYILPPPAEQLSRKDVSLTCLVVGFNPGDISVEWTSNGHT

EENYKDTAPVLDSDGSYFIYSKLDIKTSKWEKTDSFSCNVR

HEGLKNYYLKKTISRSPGK
```

The signal sequence is underlined, and the sequence of the IgG2b constant region is presented italics.

The amino acid sequence of the AB0041 light chain is as follows:

```
                                        (SEQ ID NO: 2)
MESQIQVFVFVFLWLSGVDGDIVMTQSHKFMSTSVGDRVSI

TCKASQDVRNTVAWYQQKTGQSPKLLIYSSSYRNTGVPDRF

TGSGSGTDFTFTISSVQAEDLAVYFCQQHYITPYTFGGGTK

LEIKRADAAPTVSIFPPSSEQLTSGGASVVCFLNNFYPKDI

NVKWKIDGSERQNGVLNSWTDQDSKDSTYSMSSTLTLTKDE

YERHNSYTCEATHKTSPIVKSFNRNEC
```

The signal sequence is underlined, and the sequence of the kappa constant region is presented in italics.

The following amino acid sequence comprises the framework regions and complementarity-determining regions (CDRs) of the variable region of the IgG2b heavy chain of AB0041 (with CDRs underlined):

```
                                        (SEQ ID NO: 3)
QVQLKESGPGLVAPSQSLSITCTVSGFSLLSYGVIIWVRQP

PGKGLEWLGVIWTGGTTNYNSALMSRLSISKDDSKSQVFLK

MNSLQTDDTAIYYCARYYYGMDYWGQGTSVTVSS
```

The following amino acid sequence comprises the framework regions and complementarity-determining regions (CDRs) of the variable region of the kappa light chain of AB0041 (with CDRs underlined):

```
                                        (SEQ ID NO: 4)
DIVMTQSHKFMSTSVGDRVSITCKASQDVRNTVAWYQQKTG

QSPKLLIYSSSYRNTGVPDRFTGSGSGTDFTFTISSVQAED

LAVYFCQQHYITPYTFGGGTKLEIK
```

Other exemplary mouse anti-human MMP9 antibodies (e.g., M4 and M12) are described in Example 1B. An exemplary anti-mouse MMP9 antibody (AB0046) is described in Example 1C. Other exemplary mouse anti-human MMP9 antibodies include antibodies comprise the variable regions having the sequence of SEQ ID NO: 3, and the constant regions having 95% similarity as the sequences of the IgG2b constant regions. In addition, the exemplary mouse anti-human MMP9 antibodies include antibodies comprise the variable regions having the sequence of SEQ ID NO: 4, and the constant regions having 95% similarity as the sequences of the IgG2b constant regions. Other exemplary mouse anti-human MMP9 antibodies include antibodies comprise the variable regions having the sequences of SEQ ID NOs: 3 and 4, and the constant regions having 95% similarity as the sequences of the IgG2b constant regions. Such anti-mouse antibodies are suitable for testing and assessing the MMP9-inhibition methods.

Heavy-Chain Variants

The amino acid sequences of the variable regions of the AB0041 heavy and light chains were separately modified, by altering framework region sequences in the heavy and light chain variable regions. The effect of these sequence alterations was to deplete the antibody of human T-cell epitopes, thereby reducing or abolishing its immunogenicity in humans.

Four heavy-chain variants were constructed, in a human IgG4 heavy chain background containing a S241P amino acid change that stabilizes the hinge domain (Angal et al. (1993) *Molec. Immunol.* 30:105-108), and are denoted VH1, VH2, VH3 and VH4. The amino acid sequences of their framework regions and CDRs are as follows:

```
VH1
                                        (SEQ ID NO: 5)
QVQLQESGPGLVKPSETLSLTCTVSGFSLLSYGVIIWVRQ

PPGKGLEWLGVIWTGGTTNYNSALMSRLTISKDDSKSTVY

LKMNSLKTEDTAIYYCARYYYGMDYWGQGTSVTVSS

VH2
                                        (SEQ ID NO: 6)
QVQLQESGPGLVKPSETLSLTCTVSGFSLLSYGVHWVRQP

PGKGLEWLGVIWTGGTTNYNSALMSRLTISKDDSKNTVYL

KMNSLKTEDTAIYYCARYYYGMDYWGQGTLVTVSS

VH3
                                        (SEQ ID NO: 7)
QVQLQESGPGLVKPSETLSLTCTVSGFSLLSYGVHWVRQP

PGKGLEWLGVIWTGGTTNYNSALMSRFTISKDDSKNTVYL

KMNSLKTEDTAIYYCARYYYGMDYWGQGTLVTVSS

VH4
                                        (SEQ ID NO: 8)
QVQLQESGPGLVKPSETLSLTCTVSGFSLLSYGVHWVRQP

PGKGLEWLGVIWTGGTTNYNSALMSRFTISKDDSKNTLYL

KMNSLKTEDTAIYYCARYYYGMDYWGQGTLVTVSS
```

FIG. 1 shows an alignment of the amino acid sequences of the variable regions of the humanized heavy chains and indicates the differences in amino acid sequences in the framework regions among the four variants.

Light-Chain Variants

Four light-chain variants were constructed, in a human kappa chain background, and are denoted Vk1, Vk2, Vk3 and Vk4. The amino acid sequences of their framework regions and CDRs are as follows:

```
Vk1
                                          (SEQ ID NO: 9)
DIVMTQSPSFLSASVGDRVTITCKASQDVRNTVAWYQQKT

GKAPKLLIYSSSYRNTGVPDRFTGSGSGTDFTLTISSLQA

EDVAVYFCQQHYITPYTFGGGTKVEIK

Vk2
                                         (SEQ ID NO: 10)
DIVMTQSPSSLSASVGDRVTITCKASQDVRNTVAWYQQKP

GKAPKLLIYSSSYRNTGVPDRFTGSGSGTDFTLTISSLQA

EDVAVYFCQQHYITPYTFGGGTKVEIK

Vk3
                                         (SEQ ID NO: 11)
DIQMTQSPSSLSASVGDRVTITCKASQDVRNTVAWYQQKP

GKAPKLLIYSSSYRNTGVPDRFSGSGSGTDFTLTISSLQA

EDVAVYFCQQHYITPYTFGGGTKVEIK

Vk4
                                         (SEQ ID NO: 12)
DIQMTQSPSSLSASVGDRVTITCKASQDVRNTVAWYQQKP

GKAPKLLIYSSSYRNTGVPDRFSGSGSGTDFTLTISSLQA

EDVAVYYCQQHYITPYTFGGGTKVELK
```

FIG. 2 shows an alignment of the amino acid sequences of the variable regions of the humanized light chains and indicates the differences in amino acid sequences in the framework regions among the four variants.

The humanized heavy and light chains are combined in all possible pair-wise combinations to generate a number of functional humanized anti-MMP9 antibodies. For example, provided are antibodies with a heavy chain variable (VH) region having the amino acid sequence set forth in any of SEQ ID NOs: 3, 5, 6, 7, and 8; antibodies having a light chain variable (VL) region having the amino acid sequence set forth in any of SEQ ID NOs: 4, 9, 10, 11, and 12; and antibodies with a heavy chain variable (VH) region having the amino acid sequence set forth in any of SEQ ID NOs: 3, 5, 6, 7, and 8 and a light chain variable (VL) region having the amino acid sequence set forth in any of SEQ ID NOs: 4, 9, 10, 11, and 12, as well as antibodies that compete for binding to MMP9 with such antibodies and antibodies having at least at or about 75%, 80%, 85%, 90%, 91%, 92%, 93%, 94%, 95%, 96%, 97%, 98%, 99% or more sequence identity with such antibodies. In one example, the antibody has a VII region with an amino acid sequence having at least at or about 75%, 80%, 85%, 90%, 91%, 92%, 93%, 94%, 95%, 96%, 97%, 98%, 99% or more sequence identity with SEQ ID NO: 7 and a VL region with an amino acid sequence having at least at or about 75%, 80%, 85%, 90%, 91%, 92%, 93%, 94%, 95%, 96%, 97%, 98%, 99% or more sequence identity with SEQ ID NO: 12, or a VH region of SEQ ID NO: 7 and a VI region of SEQ ID NO: 12.

Additional heavy chain variable region amino acid sequences having 75% or more, 80% or more, 90% or more, 95% or more, or 99% or more homology to the heavy chain variable region sequences disclosed herein are also provided. Furthermore, additional light chain variable region amino acid sequences having 75% or more, 80% or more, 90% or more, 95% or more, or 99% or more homology to the light chain variable region sequences disclosed herein are also provided.

Additional heavy chain variable region amino acid sequences having 75% or more, 80% or more, 90% or more, 95% or more, or 99% or more sequence identity to the heavy chain variable region sequences disclosed herein are also provided. Furthermore, additional light chain variable region amino acid sequences having 75% or more, 80% or more, 90% or more, 95% or more, or 99% or more sequence identity to the light chain variable region sequences disclosed herein are also provided.

Complementarity-Determining Regions (CDRs)

In some embodiments, the CDRs of the heavy chain of exemplary provided anti-MMP9 antibodies as disclosed herein have the following amino acid sequences:

```
CDR1:
                                         (SEQ ID NO: 13)
GFSLLSYGVH

CDR2:
                                         (SEQ ID NO: 14)
VIWTGGTTNYNSALMS

CDR3:
                                         (SEQ ID NO: 15)
YYYGMDY
```

Thus, among the provided anti-MMP9 antibodies are antibodies having a heavy chain CDR1 region with an amino acid sequence as set forth in SEQ ID NO: 13, antibodies having a heavy chain CDR2 region with an amino acid sequence set forth in SEQ ID NO: 14, and antibodies having a heavy chain CDR3 region with an amino acid sequence as set forth in SEQ ID NO: 15, and antibodies that compete for binding with or bind to the same epitope on MMP9 as such antibodies. In some cases, the antibodies contain VH CDRs having the sequences set forth in SEQ ID NO: 13, 14, and 15.

In some embodiments, the CDRs of the light chain of exemplary anti-MMP9 antibodies as disclosed herein have the following amino acid sequences:

```
CDR1:
                                         (SEQ ID NO: 16)
KASQDVRNTVA

CDR2:
                                         (SEQ ID NO: 17)
SSSYRNT

CDR3:
                                         (SEQ ID NO: 18)
QQHYITPYT
```

Thus, among the provided anti-MMP9 antibodies are antibodies having a light chain CDR1 region with an amino acid sequence as set forth in SEQ ID NO: 16, antibodies having a light chain CDR2 region with an amino acid sequence set forth in SEQ ID NO: 17, and antibodies having a light chain CDR3 region with an amino acid sequence as set forth in SEQ ID NO: 18, and antibodies that compete for binding with or bind to the same epitope on MMP9 as such antibodies. In some cases, the antibodies contain VL CDRs having the sequences set forth in SEQ ID NO: 16, 17, and 18.

Nucleic Acids Encoding Anti-MMP9 Antibodies

The present disclosure provides nucleic acids encoding anti-MMP9 antibodies and functional fragments thereof. Accordingly, the present disclosure provides an isolated polynucleotide (nucleic acid) encoding an antibody or antigen-binding fragment as described herein, vectors containing such polynucleotides, and host cells and expression systems for transcribing and translating such polynucleotides into polypeptides.

The present disclosure also contemplates constructs in the form of plasmids, vectors, transcription or expression cassettes which comprise at least one polynucleotide as above.

The present disclosure also provides a recombinant host cell which comprises one or more constructs as above, as well as methods of production of the antibody or antigen-binding fragments thereof described herein which method comprises expression of nucleic acid encoding a heavy chain polypeptide and a light chain polypeptide (in the same or different host cells, and from the same or different constructs) in a recombination host cell. Expression can be achieved by culturing under appropriate conditions recombinant host cells containing the nucleic acid. Following production by expression, an antibody or antigen-binding fragment can be isolated and/or purified using any suitable technique, then used as appropriate.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common bacterial host is *E. coli*.

Suitable vectors can be chosen or constructed, containing appropriate regulatory sequences, including operably linked promoter sequences, terminator sequences, polyadenylation sequences, enhancer sequences, marker genes and/or other sequences as appropriate. Vectors can be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The disclosures of Sambrook et al. and Ausubel et al. are incorporated herein by reference in their entirety.

The nucleic acid encoding a polypeptide of interest is integrated into the genome of the host cell or can be maintained as a stable or transient episomal element.

Any of a wide variety of expression control sequences—sequences that control the expression of a DNA sequence operatively linked to it—can be used in these vectors to express the DNA sequences. For example, a nucleic acid encoding a polypeptide of interest can be operably linked to a promoter, and provided in an expression construct for use in methods of production of recombinant MMP9 proteins or portions thereof.

Those of skill in the art are aware that nucleic acids encoding the antibody chains disclosed herein can be synthesized using standard knowledge and procedures in molecular biology.

Examples of nucleotide sequences encoding the heavy and light chain amino acid sequences disclosed herein, are as follows:

VH1:
(SEQ ID NO: 19)
CAGGTGCAGC TGCAGGAATC CGGCCCTGGC CTGGTCAAGC

CCTCCGAGAC ACTGTCCCTC ACCTGCACCG TGTCCGGCTT

CTCCCTGCTG TCCTACGGCG TGCACTGGGT CCGACAGCCT

CCAGGGAAGG GCCTGGAATG GCTGGGCGTG ATCTGGACCG

GCGGCACCAC CAACTACAAC TCCGCCCTGA TGTCCCGGCT

GACCATCTCC AAGGACGACT CCAAGTCCAC CGTGTACCTG

AAGATGAACT CCCTGAAAAC CGAGGACACC GCCATCTACT

ACTGCGCCCG GTACTACTAC GGCATGGACT ACTGGGGCCA

GGGCACCTCC GTGACCGTGT CCTCA

VH2:
(SEQ ID NO: 20)
CAGGTGCAGC TGCAGGAATC CGGCCCTGGC CTGGTCAAGC

CCTCCGAGAC ACTGTCCCTG ACCTGCACCG TGTCCGGCTT

CTCCCTGCTG TCCTACGGCG TGCACTGGGT CCGACAGCCT

CCAGGCAAAG GCCTGGAATG GCTGGGCGTG ATCTGGACCG

GCGGCACCAC CAACTACAAC TCCGCCCTGA TGTCCCGGCT

GACCATCTCC AAGGACGACT CCAAGAACAC CGTGTACCTG

AAGATGAACT CCCTGAAAAC CGAGGACACC GCCATCTACT

ACTGCGCCCG GTACTACTAC GGCATGGACT ACTGGGGCCA

GGGCACCCTG GTCACCGTGT CCTCA

VH3:
(SEQ ID NO: 21)
CAGGTGCACC TGCAGGAATC CGGCCCTCGC CTGGTCAAGC

CCTCCGAGAC ACTGTCCCTG ACCTGCACCG TGTCCGGCTT

CTCCCTGCTG TCCTACGGCG TGCACTGGGT CCGACAGCCT

CCAGGCAAAG GCCTGGAATG GCTGGGCGTG ATCTGGACCG

GCGGCACCAC CAACTACAAC TCCGCCCTGA TGTCCCGGTT

CACCATCTCC AAGGACGACT CCAAGAACAC CGTGTACCTG

AAGATGAACT CCCTGAAAAC CGAGGACACC GCCATCTACT

ACTGCGCCCG GTACTACTAC GGCATGGACT ACTGGGGCCA

GGGCACCCTG GTCACCGTGT CCTCA

VH4:
(SEQ ID NO: 22)
CAGGTGCAGC TGCAGGAATC CGGCCCTGGC CTGGTCAAGC

CCTCCGAGAC ACTGTCCCTG ACCTGCACCG TGTCCGGCTT

CTCCCTGCTG TCCTACGGCG TGCACTGGGT CCGAGAGCCT

CCAGGCAAAG GCCTGGAATG GCTGGGCGTG ATCTGGACCG

GCGGCACCAC CAACTACAAC TCCGCCCTGA TGTCCCGGTT

CACCATCTCC AAGGACGACT CCAAGAACAC CCTGTACCTG

AAGATGAACT CCCTGAAAAC CGAGGACACC GGCATCTACT

ACTGCGCCCG GTACTACTAC GGCATGGACT ACTGGGGCCA

GGGCACCCTG GTCACCGTGT CCTCA

Vk1:
(SED ID NO: 23)
GACATCGTGA TGACCCAGTC CCCCAGCTTC CTGTCCGCCT

CCGTGGGCGA CAGAGTGACC ATCAGATGCA AGGCCTCTCA

GGACGTGCGG AACACCGTGG CCTGGTATCA GCAGAAACCC

-continued

```
GGCAAGGCCC CCAAGCTGCT GATCTACTCC TCCTCCTACC

GGAACACCGG CGTGCCCGAC CGGTTTACCG GCTCTGGGTC

CGGCACCGAC TTTACCCTGA CCATCAGCTC CCTGCAGGCC

GAGGACGTGG CCGTGTACTT CTGCCAGCAC CACTACATCA

CCCCCTACAC CTTCGGCGGA GGCACCAAGG TGGAAATAAA

A
```

Vk2:
(SEQ ID NO: 24)
```
GACATCGTGA TGACCCAGTC CCCCTCCAGC CTGTCCGCCT

CTGTGGGCGA CAGAGTGACC ATCACATGCA AGGCCTCTCA

GGACGTGCGG AACACCGTGG CCTGCTATCA GCAGAAGCCC

GGCAAGGCCC CCAAGCTGCT GATCTAGTCC TCCTCCTACC

GGAACACCGC CCTCCCCGAC CGGTTTACCC GCTCTGGCTC

CGGCACCGAC TTTACCCTGA CCATCAGCTC CCTGCAGGCC

GAGGACGTGG CCGTGTACTT CTGCCAGCAG CACTACATCA

CCCCCTACAC CTTCGGCGGA GGCACCAAGG TGGAAATAAA

A
```

Vk3:
(SEQ ID NO: 25)
```
GACATCCACA TGACCCAGTC CCCCTCCAGC CTGTCCGCCT

CTGTGGGCGA CAGAGTGACC ATCACATGCA AGGCCTCCCA

GGACGTGCGG AACACCGTGG CCTGGTATCA GCAGAAGCCC

GGCAAGGCCC CCAAGCTGCT GATCTACTGC TCCTCCTACC

GGAACAGCGG CGTGCCCGAC CGGTTCTCTG GCTCTGGAAG

CGGCACCGAC TTTACCCTGA CCATCAGCTC CCTGCAGGCC

GAGGACGTGG CCGTGTACTT CTGCCAGCAG CACTACATCA

CCCCCTACAC CTTCGGCGGA GGCACCAAGG TGGAAATAAA

A
```

Vk4:
(SEQ ID NO: 26)
```
GACATCCAGA TGACCCAGTC CCCCTCCAGC CTGTCCGCCT

CTGTGGGCGA CAGAGTGACC ATCACATGCA AGGCCTCTCA

GGACGTGCGG AACACCGTGG CCTGGTATCA GCAGAAGCCC

GGCAAGGCCC CCAAGCTGCT GATCTACTCC TCCTCCTACC

GGAAGACCGG CGTGCCCGAC CGGTTCTCTG GCTCTGGAAG

CGGCACCGAC TTTACCCTGA CCATCAGCTC CCTGCAGGCC

GAGGACGTGG CCGTGTACTA CTGCCAGCAG CACTACATCA

CCCCCTACAC CTTCGGCGGA GGCACCAAGG TGGAAATAAA

A
```

Because the structure of antibodies, including the juxtaposition of CDRs and framework regions in the variable region, the structure of framework regions and the structure of heavy- and light-chain constant regions, is well-known in the art; it is well within the skill of the art to obtain related nucleic acids that encode anti-MMP-9 antibodies. Accordingly, polynucleotides comprising nucleic acid sequences having at least 75%, at least 80%, at least 85%, at least 90%, at least 95%, at least 98% and at least 99% homology to any of the nucleotide sequences disclosed herein are also provided. Accordingly, polynucleotides comprising nucleic acid sequences having at least 75%, at least 80%, at least 85%, at least 90%, at least 95%, at least 98% and at least 99% identity to any of the nucleotide sequences disclosed herein are also provided. In one example, the polynucleotide contains at least at or about 75%, 80%, 85%, 90%, 91%, 92%, 93%, 94%, 95%, 96%, 97%, 98%, 99% or more sequence identity with SEQ ID NO: 21 or includes or is SEQ ID NO: 21 and/or contains at least at or about 75%, 80%, 85%, 90%, 91%, 92%, 93%, 94%, 95%, 96%, 97%, 98%, 99% or more sequence identity with SEQ ID NO: 26 or includes or is SEQ ID NO: 26.

Pharmaceutical Compositions

MMP9 binding proteins, as well as nucleic acid (e.g., DNA or RNA) encoding MMP9 binding proteins, can be provided as a pharmaceutical composition, e.g., combined with a pharmaceutically acceptable carrier or excipient. Such pharmaceutical compositions are useful for, for example, administration to a subject in vivo or ex vivo, and for diagnosing and/or treating a subject with the MMP9 binding proteins, such as in any of the therapeutic or diagnostic methods provided herein.

Pharmaceutically acceptable carriers are physiologically acceptable to the administered patient and retain the therapeutic properties of the antibodies or peptides with which it is administered. Pharmaceutically-acceptable carriers and their formulations are and generally described in, for example, Remington' pharmaceutical Sciences (18th Edition, ed. A. Gennaro, Mack Publishing Co., Easton, Pa. 1990). One exemplary pharmaceutical carrier is physiological saline. Each carrier is "pharmaceutically acceptable" in the sense of being compatible with the other ingredients of the formulation and not substantially injurious to the patient.

Pharmaceutical compositions can be formulated to be compatible with a particular route of administration, systemic or local. Thus, pharmaceutical compositions include carriers, diluents, or excipients suitable for administration by various routes.

Pharmaceutical compositions can include pharmaceutically acceptable additives. Examples of additives include, but are not limited to, a sugar such as mannitol, sorbitol, glucose, xylitol, trehalose, sorbose, sucrose, galactose, dextran, dextrose, fructose, lactose and mixtures thereof. Pharmaceutically acceptable additives can be combined with pharmaceutically acceptable carriers and/or excipients such as dextrose. Additives also include surfactants such as polysorbate 20 or polysorbate 80.

The formulation and delivery methods will generally be adapted according to the site and the disease to be treated. Exemplary formulations include, but are not limited to, those suitable for parenteral administration, e.g., intravenous, intra-arterial, intramuscular, or subcutaneous administration, or oral administration.

Pharmaceutical compositions for parenteral delivery include, for example, water, saline, phosphate buffered saline, Hank's solution, Ringer's solution, dextrose/saline, and glucose solutions. The formulations can contain auxiliary substances to approximate physiological conditions, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. Additional parenteral formulations and methods are described in Bai (1997) J. Neuroimmunol. 80:65 75; Warren (1997) J. Neurol. Sci. 152:3138; and Tonegawa (1997) J. Exp. Med. 186:507 515. The parenteral preparation can be enclosed in ampules, disposable syringes or multiple dose vials made of glass or plastic.

Pharmaceutical compositions for intradermal or subcutaneous administration can include a sterile diluent, such as water, saline solution, fixed oils, polyethylene glycols, glycerine, propylene glycol or other synthetic solvents; antibacterial agents such as benzyl alcohol or methyl parabens; antioxidants such as ascorbic acid, glutathione or sodium bisulfite; chelating agents such as ethylenediaminetetraacetic acid; buffers such as acetates, citrates or phosphates and agents for the adjustment of tonicity such as sodium chloride or dextrose.

Pharmaceutical compositions for injection include aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. Fluidity can be maintained, for example, by the use of a coating such as lecithin, by the maintenance of the required particle size in the case of dispersion and by the use of surfactants. Antibacterial and antifungal agents include, for example, parabens, chlorobutanol, phenol, ascorbic acid and thimerosal. Isotonic agents, for example, sugars, polyalcohols such as manitol, sorbitol, and sodium chloride may be included in the composition. The resulting solutions can be packaged for use as is, or lyophilized; the lyophilized preparation can later be combined with a sterile solution prior to administration.

Pharmaceutically acceptable carriers can contain a compound that stabilizes, increases, or delays absorption or clearance. Such compounds include, for example, carbohydrates, such as glucose, sucrose, or dextrans; low molecular weight proteins; compositions that reduce the clearance or hydrolysis of peptides; or excipients or other stabilizers and/or buffers. Agents that delay absorption include, for example, aluminum monostearate and gelatin. Detergents can also be used to stabilize or to increase or decrease the absorption of the pharmaceutical composition, including liposomal carriers. To protect from digestion the compound can be complexed with a composition to render it resistant to acidic and enzymatic hydrolysis, or the compound can be complexed in an appropriately resistant carrier such as a liposome. Means of protecting compounds from digestion are known in the art (see, e.g., Fix (1996) Pharm Res. 13:1760 1764; Samanen (1996) J. Pharm. Pharmacol. 48:119 135; and U.S. Pat. No. 5,391,377, describing lipid compositions for oral delivery of therapeutic agents).

Compositions of the present invention can be combined with other therapeutic moieties or imaging/diagnostic moieties as provided herein. Therapeutic moieties and/or imaging moieties can be provided as a separate composition, or as a conjugated moiety present on an MMP9 binding protein.

Formulations for in vivo administration are generally sterile. In one embodiment, the pharmaceutical compositions are formulated to be free of pyrogens such that they are acceptable for administration to human patients.

Various other pharmaceutical compositions and techniques for their preparation and use will be known to those of skill in the art in light of the present disclosure. For a detailed listing of suitable pharmacological compositions and associated administrative techniques one can refer to the detailed teachings herein, which can be further supplemented by texts such as Remington: The Science and Practice of Pharmacy 20th Ed. (Lippincott, Williams & Wilkins 2003).

Pharmaceutical compositions can be formulated based on the physical characteristics of the patient/subject needing treatment, the route of administration, and the like. Such can be packaged in a suitable pharmaceutical package with appropriate labels for the distribution to hospitals and clinics wherein the label is for the indication of treating a disorder as described herein in a subject. Medicaments can be packaged as a single or multiple units. Instructions for the dosage and administration of the pharmaceutical compositions of the present invention can be included with the pharmaceutical packages and kits described below.

Methods of Use

The MMP9 binding proteins, including anti-MMP9 antibodies and fragments thereof, of the present disclosure can be used, for example, in therapeutic and diagnostic methods, such as methods of detection of MMP9 in a sample, methods of treatment (e.g., as in methods of inhibition of angiogenesis), and methods of diagnosis and prognosis. Thus, provided are diagnostic and therapeutic methods and uses of the anti-MMP9 antibodies. Examples of methods of use are described below.

Methods of Treatment

Provided herein are methods of treatment, including methods of treating diseases and disorders associated with MMP9 expression and/or activity, as well as uses of the provided antibodies and compositions in such methods. The diseases and disorders include, but are not limited to cancer, e.g., tumors (e.g., primary or metastatic tumors), such as those that express or are disposed in a tissue which expresses MMP9, and inflammatory diseases, such as inflammatory bowel diseases, rheumatoid arthritis and inflammatory myopathies.

As used herein, "treat" or "treatment" means stasis or a postponement of development of one or more symptoms associated with a disease or disorder described herein, or ameliorating existing uncontrolled or unwanted symptoms, preventing additional symptoms, or ameliorating or preventing the underlying metabolic causes of symptoms. Thus, the terms denote that a beneficial result has been conferred on a mammalian subject with a disease or symptom, or with the potential to develop such disease or symptom. A response is achieved when the patient experiences partial or total alleviation, or reduction of signs or symptoms of illness, and can include, without limitation, prolongation of survival. The expected progression-free survival times can be measured in months to years, depending on prognostic factors including the number of relapses, stage of disease, and other factors.

Also provided are pharmaceutical compositions for use in connection with such methods, such as those containing any of the antibodies or fragments thereof described herein. Compositions can be suitable for administration locally or systemically by any suitable route.

In general, MMP9 binding proteins are administered in a therapeutically effective amount, e.g., in an amount to effect inhibition of tumor growth in a subject, to inhibit metastasis, to inhibit inflammation, to inhibit tissue destruction, to inhibit MMP9 activity, or to treat the particular disease or condition associated with MMP9.

As used herein, unless otherwise specified, the term "therapeutically effective amount" or "effective amount"

refers to an amount of an agent or compound or composition that when administered (either alone or in combination with another therapeutic agent, as may be specified) to a subject is effective to prevent or ameliorate the disease condition or the progression of the disease, or result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. In one example, when in vivo administration of an anti-MMP9 antibody is employed, normal dosage amounts can vary from about 10 ng/kg to up to 100 mg/kg of mammal body weight or more per day, preferably about 1 µg/kg/day to 50 mg/kg/day, optionally about 100 µg/kg/day to 20 mg/kg/day, 500 µg/kg/day to 10 mg/kg/day, or 1 mg/kg/day to 10 mg/kg/day, depending upon the route of administration. In one embodiment, intravenous dosage range from about 1 mg/kg to about 30 mg/kg. In some embodiments, intravenous dosages range from at or about 1 mg/kg to at or about 14 mg/kg, such as from at or about 2 mg/kg to at or about 14 mg/kg, q14d, once every 14 days. In other embodiments, subcutaneous dosages range from at or about 1 mg/kg to at or about 28 mg/kg, such as from at or about 2 mg/kg to at or about 28 mg/kg, q14d, once every 14 days. In some embodiments, the effective amount of dosage is administered once every 7 to 28 days. In one embodiment, the effective amount of dosage is administered once every 7 days. In another embodiment, the effective amount of dosage is administered once every 28 days.

The selected dosage regimen will depend upon a variety of factors including the activity of the MMP9 binding protein, the route of administration, the time of administration, the rate of excretion of the particular compound being employed, the duration of the treatment, other drugs, compounds and/or materials used in combination with the particular composition employed, the age, sex, weight, condition, general health and prior medical history of the patient being treated, and like factors well known in the medical arts.

A clinician having ordinary skill in the art can readily determine and prescribe the effective amount of the pharmaceutical composition required. For example, the physician or veterinarian can start doses of the compounds of the invention employed in the pharmaceutical composition at levels lower than that required in order to achieve the desired therapeutic effect and gradually increase the dosage until the desired effect is achieved.

In some cases, the methods of treatment include parenteral administration, e.g., intravenous, intra-arterial, intramuscular, or subcutaneous administration, or oral administration of the agent, e.g., anti-MMP9 antibody or composition containing the same.

As used herein, the term "subject" means a mammalian subject. Exemplary subjects include, but are not limited to humans, monkeys, dogs, cats, mice, rats, cows, horses, goats and sheep. In some embodiments, the subject has cancer, an inflammatory disease or condition, or an autoimmune disease or condition, and can be treated with the agent of the present invention as described below.

If needed, for treatments, methods can further include additional therapies, such as in the case of cancer, surgical removal of the cancer and/or administration of an anti-cancer agent or treatment in addition to an MMP9 binding protein. Administration of such an anti-cancer agent or treatment can be concurrent with administration of the compositions disclosed herein.

Methods of Detection of MMP9

The present disclosure also contemplates methods of detecting MMP9 in a subject, e.g., to detect tumor or tumor-associated tissue expressing MMP9, or tissue or fluid or other biological sample associated with a disease as described herein, such as autoimmune or inflammatory disease. Thus, methods of diagnosing, monitoring, staging or detecting a tumor having MMP9 activity are provided.

Samples (e.g., test biological samples) from a subject (e.g., an individual suspected of having or known to have a tumor associated with MMP9 expression, or suspected of having or known to have another disease or condition), can be analyzed for MMP9 presence, absence, expression, and/or levels. For example, such samples can be collected and analyzed by detecting the presence or absence of binding of an MMP9 binding protein, such as an antibody or fragment as described herein, to substance (e.g., protein) in the sample. In some examples, the methods further include comparing the amount of binding detected to an amount of binding to a control sample, or comparing the detected level of MMP9 to a control level of MMP9. In some cases, the methods indicate the presence, absence, or severity of an MMP9-associated disease or condition, such as one described herein.

This analysis can be performed prior to the initiation of treatment using an MMP9 binding protein as described herein, or can be done as part of monitoring of progress of cancer treatment. In some embodiments, provided are methods of treatment, carried out by performing the detection assays and initiating, altering, or discontinuing treatment of the subject, for example, based on the results of the diagnostic assay. Such diagnostic analysis can be performed using any sample, including but not limited to tissue, cells isolated from such tissues, and the like. In some cases, the methods are performed on liquid samples, such as blood, plasma, serum, whole blood, saliva, urine, or semen. Tissue samples include, for example, formalin-fixed or frozen tissue sections.

Any suitable method for detection and analysis of MMP9 can be employed. Various diagnostic assay techniques known in the art can be adapted for such purpose, such as competitive binding assays, direct or indirect sandwich assays and immunoprecipitation assays conducted in either heterogeneous or homogeneous phases.

MMP9 binding proteins for use in detection methods can be labeled with a detectable moiety. The detectable moiety directly or indirectly produces a detectable signal. For example, the detectable moiety can be any of those described herein such as, for example, a radioisotope, such as 3H, 14C, 32P, 35S, or 125I, a fluorescent or chemiluminescent compound, such as fluorescein isothiocyanate (FITC), Texas red, cyanin, photocyan, rhodamine, or luciferin, or an enzyme, such as alkaline phosphatase, β-galactosidase or horseradish peroxidase.

Detection can be accomplished by contacting a sample under conditions suitable for MMP9 binding protein binding to MMP9, and assessing the presence (e.g., level) or absence of MMP9 binding protein-MMP9 complexes. A level of MMP9 in the sample in comparison with a level of a reference sample can indicate the presence of a tumor or tumor-associated tissues having MMP9 activity. The reference sample can be a sample taken from the subject at an earlier time point or a sample from another individual.

Various aspects of the invention are further described and illustrated by way of the several examples which follow, none of which are intended to limit the scope of the invention.

EXAMPLES

Example 1A: Preparation of Antibodies to Human MMP-9

The full-length human MMP9 protein without a signal peptide (SEQ ID NO. 28) was used to immunize mice. Spleen cells from immunized mice were fused with myeloma cells to generate a hybridoma library. Monoclonal cultures were prepared and screened to identify cultures expressing an anti-MMP9 monoclonal antibody.

An antibody (AB0041) was purified from one of the cultures and characterized. This antibody contained an IgG2b heavy chain and a kappa light chain. Characterization included testing for the binding of AB0041 to other human MMPs and to MMP9 proteins from other species, including cynomolgus monkey, rat and mouse. As shown in Table 2, the AB0041 antibody had greater affinity to human and cynomolgus MMP9, that it had lower affinity to rat MMP9. In addition, the AB0041 antibody did not bind to murine MMP9 or to many human non-MMP matrix metalloproteinases.

TABLE 2

| MMP Tested | Dissociation constant (Kd) | |
| --- | --- | --- |
|  | AB0045 | AB0041 |
| Human MMP1 | >100 nM | >100 nM |
| Human MMP2 | >100 nM | >100 nM |
| Mouse MMP2 | >100 nM | >100 nM |
| Human MMP3 | >100 nM | >100 nM |
| Human MMP7 | >100 nM | >100 nM |
| Human MMP8 | >100 nM | >100 nM |
| Human MMP9 | 0.168 ± 0.117 nM | 0.133 ± 0.030 nM |
| Cynomolgus monkey MMP9 | 0.082 ± 0.022 nM | 0.145 ± 0.16 nM |
| Mouse MMP9 | >100 nM | >100 nM |
| Rat MMP9 | 0.311 ± 0.017 nM | 0.332 ± 0.022 nM |
| Human MMP10 | >100 nM | >100 nM |
| Human MMP12 | >100 nM | >100 nM |
| Human MMP13 | >100 nM | >100 nM |

Additional characterization included assaying the binding of AB0041 to mutant mouse and human MMP9 proteins. Non-identical residues in the catalytic domain of mouse and human MMP9 proteins were identified, and forty-six non-identical amino acid residues were selected for mutagenesis. Most mutations were generated in mouse MMP9: the mouse amino acid residues were mutated to match those of human MMP9. Other mutations were generated in human MMP9: the human amino acid residues were mutated to match those of mouse MMP9. The mutated mouse or human MMP9 proteins were used in an ELISA assay.

In the ELISA assay, the AB0041 antibody was used as the primary antibody and a goat anti-mouse IgG antibody conjugated to horseradish peroxidase was used to detect the binding. The wild-type human MMP9 was used a positive control and the wild-type mouse MMP9 was used as a negative control. The results of the ELISA assay showed an arginine residue at position 162 of the MMP9 amino acid sequence (R162) as important for the MMP9 binding of the AB0041 antibody. The results also showed the amino acid residues E111, D113, and I198 were important for the MMP9 binding of the AB0041 antibody. Based on the crystal structure of MMP9, E111, D113, R162, and I198 are grouped near each other around a Ca2+ ion binding pocket of MMP9. In this study, the AB0041 antibody was shown to specifically bind to an epitope containing amino acid residues within regions of MMP9 containing amino acid residues 104-119, 159-166, and 191-202.

In an enzymatic assay for MMP9, the AB0041 antibody was found to act as a non-competitive inhibitor of MMP9.

Example 1B: Preparation of Additional Antibodies to Human MMP-9

Additional hybridomas were generated, which produced antibodies having variable regions that shared identity with AB0041. One such hybridoma, designated M4, expressed an antibody containing the heavy chain (IgG2b) sequence:

(SEQ ID NO: 30)
MAVLVLFLCLVAFPSCVLSQVQLKESGPGLVAPSQSLSITCTVSGFSLLS

YGVHWVRQPPGKGLEWLGVIWTGGSTNYNSALMSRLSISKDDSKSQVFLK

MNSLQTDDTAMYYCARYYYAMDYWGQGTSVTVSSAKTTPPSVYPLAPGCG

DTTGSSVTLGCLVKGYFPESVTVTWNSGSLSSSVHTFPALLQSGLYTMSS

SVTVPSSTWPSQTVTCSVAHPASSTTVDKKLEPSGPISTINPCPPCKECH

KCPAPNLEGGPSMFPPNIKDVLMISLTPKVTVVVDVSEDDPDVRISWFVN

NVEVHTAQTQTHREDYNSTIRVVSALPIQHQDWMSGKEFKCKVNNKDLPS

PIERTISKIKGLVRAPQVYILPPPAEQLSRKDVSLTCLVVGFNPGDISVE

WTSNGHTEENYKDTAPVLDSDGSYFIYSKLDIKTSKWEKTDSFSCNVRHE

GLKNYYLKKTISRSPGK (signal peptide set forth in underlined text, variable region set forth in plain text, and constant region set forth in italics), and the light chain (kappa) sequence:

(SEQ ID NO: 31)
MESQIQVFVFVFLWLSGVDGDIVMTQSHKFMFTSVGDRVSITCKASQDVR

NTVAWYQQKTGQSPKLLIYSASYRNTGVPDRFTGSISGTDFTFTISSVQA

EDLALYYCQQHYSTPYTFGGGTKLEVKRADAAPTVSIFPPSSEQLTSGGA

SVVCFLNNFYPKDINVKWKIDGSERQNGVLNSWTDQDSKDSTYSMSSTLT

LTKDEYERHNSYTCEATHKTSTSPIVKSFNRNEC
(signal peptide set forth in underlined text,
variable region set forth in plain text, and
constant region set forth in italics).

The M4 antibody had a variable heavy chain with an amino acid sequence:

(SEQ ID NO: 32)
QVQLKESGPGLVAPSQSLSITCTVSGFSLLSYGVHWRQPPGKGLEWLGVI

WTGGSTNYNSALMSRLSISKDDSKSQVFLKMNSLQTDDTAMYYCARYYYA

MDYWGQGTSVTVSS CDRs 1, 2, and 3 (SEQ ID NOs: 34,
35, and 36, respectively) underlined)

and a variable light chain with the amino acid sequence (SEQ ID NO: 33)
DIVMTQSHKEMFTSVGDRVSITC<u>KASQDVRNTVA</u>WYQOKTGQSPKLLIY<u>S</u>

<u>ASYRNT</u>GVPDRFTGSISGTDFTFTISSVQAEDLALYYC<u>QQHYSTPYT</u>FGG

GTKLEVK (CDRs 1, 2, and 3 (SEQ. ID NOs: 37, 38,
and 39, respectively) underlined).

Another such hybridoma, designated M12, expressed only a kappa chain, having the sequence:

(SEQ ID NO: 40)
<u>QVFVYMLLWLSGVDGD</u>IVMTQSQKFMSTSVGDRVSVTCKASQNVGTNVA

WYQQKPGQSPKALIYSASYRFSGVPDRFTGSGSGTDFLTISNVQSEDLAE

YFCQQYNSYPYTFGGGTKLEIK*RADAAPTVSIPPPSSEQLTSGGASVVCF*

*LNNFYPKDINVKWKIDGSERQNGVLNSWTDQDSKDSTYSMSSTLTLTKDE*

*YERHNSYTCEATHKTSTSPIVKSFNRNEC* (signal peptide set
forth in underlined text., variable region set
forth in plain text, and constant region set forth
in italics).

The M12 antibody had a variable light chain with the amino acid sequence (SEQ ID NO: 41)
DIVMTQSQKFMSTSVGDRVSVTC<u>KASQNVGTNVA</u>WYQQKPGQPKALIY<u>SA</u>

<u>SYRF</u>SGVPDRFTGSGSGTDFTLTISNVQSEDLAEYFC<u>QQYNSYPYT</u>FGGG

TKLEIK (CDRs 1, 2, and 3 (SEQ ID NOs: 42, 43, and
44, respectively) underlined).

A sequence comparison, showing differences between the M4 and M12 heavy and light chains as compared with AB0041 antibody is shown in FIG. 4.

An enzymatic assay was carried out. The results demonstrated that the antibodies produced by the M4 and M12 hybridomas acted as non-competitive inhibitors of MMP9 (data not shown).

Example 1C: Preparation of Antibodies to Mouse MMP-9

Another mouse antibody, AB0046, was generated. Using a process similar to that described in Example 1A, the MMP9-knockout mice (strain B6.FVB (Cg)-Mmp9$^{tm1Tvu}$/J) was immunized using targeted domains of the pro/catalytic domain fragment of murine MMP9. The AB0046 antibody had a kappa light chain with an amino acid sequence (SEQ ID NO: 45)
<u>MSSAQFLGLLLLCFQGTRC</u>DIQMTQTTSSLSASLGDRVTISCSASQGISN

YLNWYQQKPDGTFKLLIYYTSILIISGVPSRFSGSGSGTDYSLTISNLEP

EDIATYYCQQYGWLPRTFGGGTKLEIK*RADAAPTVSIFPPSSEQLTSGGA*

*SVVCFLNNFYPKDINVKWKIDGSERQNGVLNSWTDQDSKDSTYSMSSTLT*

*LTKDEYERHNSYTCEATHKTSTSPIVKSFNRNEC*

(signal peptide set forth in underlined text, variable region set forth in plain text, and constant region set forth in italics) and an IgG1 heavy chain with an amino acid sequence (SEQ ID NO: 46)
<u>MGWSSIILFLTVATATGVHSQ</u>VQLQQPGSVLVRPGASVKLSCTASGYTFT

SYWMNWVKQRPGQGLEWIGEIYPISGRTNYNEKFKVKATLTVDTSSSTAY

MDLNSLTSEDSAVYYCARSRANWDDYWGQGVTTLTVSS*AKTTPPSVYPLA*

*PGSAAQTNSMLGCLVKGYFPEPVTVTWNSGSLSSGVHIPPAVLQSDLYIL*

*SSSVTVPSSTWPSETITCNVAHPASSITKVDKKIVTRDCGCKPCICTVPE*

*VSSVFIFPPKPKDVLTTTLTPKVTCVVVDISKDDPEVQFSWFVDDVEVHT*

*AQTQPREEQFNSTFRSVSELPIMHQWLNGKEFKCRVNSAAFPAPIEKTIS*

*KTKGRPKAPQVYTIPPPKEQMAKDKVSLTCMITDFFPEDITVEWQWNGQP*

*AENYKNTPIMDTDGSYFVYSKLNVQKSNWEAGNTFTCSVLHEGLHNHHTE*

*KSLSHSPGK* (signal peptide set forth in underlined
text, variable region set forth in plain text, and
constant region set forth in italics).

The following amino acid sequence comprises the framework regions and complementarity-determining regions (CDRs) of the variable region of the IgG1 heavy chain of AB0046 (with CDRs underlined):

(SEQ ID No: 47)
QVQLQQPGSVLVRPGASVKLSCTAS<u>GYTFTSYWMN</u>WVKQRPGQGLEWIG<u>EI</u>

<u>YPISGRTNYNEKFKV</u>KATLTVDTSSSTAYMDLNSLTSEDSAVYYCAR<u>SRAN</u>

<u>WDDY</u>WGQGTTLTVSS.

The following amino acid sequence comprises the framework regions and complementarity-determining regions (CDRs) of the variable region of the kappa light chain of AB0046 (with CDRs underlined):

(SEQ ID No: 48)
DIQMTQTTSSLSASLGDRVTISC<u>SASQGISNYLN</u>WYQQKPDGTFKLLIY<u>YT</u>

<u>SILHS</u>GVPSRFSGSGSGTDYSLTISNLEPEDIATYYC<u>QQYGWIPRT</u>FGGGT

KLEIK

Additional characterizations showed that the AB0046 antibody bound to mouse MMP9 non-competitively or its binding was not dependent on the concentration of mouse MMP9. The AB0046 antibody did not bind to human MMP9 or MMP2, mouse MMP2, 3, 7, 8, or 12. Using epitope analysis as described in Example 1A, it was shown that the proline residue at position 162 of the mouse MMP9 amino acid sequence (P162) (corresponding to R162 of human MMP9) was important for the MMP9 binding of the AB0046 antibody. The results suggested that the AB0046 antibody specifically bound to an epitope containing a residue within a portion of mouse MMP9 corresponding to the portion containing amino acids 159-166 of human MMP9. Thus, the AB0046 antibody was an inhibitory antibody specific to mouse MMP9 and had similar kinetics of binding and inhibition as those of AB0041. Because AB0046 is specific to mouse MMP9 and binds to an epitope as AB0041/AB0045, AB0046 is suitable for assays which uses either AB0041 or AB0045.

Further characterization showed that the AB0046 antibody was a murine IgG1 isotype, having a limited effector function in mouse.

Three other mouse anti-MMP9 antibodies were generated using similar methods, which were non-inhibitory and for which P162 was important for binding.

Example 2: Humanization of Antibodies to Human MMP9

The amino acid sequences of the heavy chain and light chain of the mouse AB0041 antibody were altered at certain locations in the framework (i.e., non-CDR) portion of their variable regions to generate proteins that are less immunogenic in humans. These amino acid sequence changes were shown in FIGS. 1 and 2. The cross-reactivity of one humanized antibody, referred to as AB0045, is shown in Table 2A above.

The humanized variant anti-MMP9 antibody, AB0045 (humanized, modified IgG4 (S241P); see Example 2, above) contained the humanized AB0041 heavy chain variant VH3 (having the sequence set forth in SEQ ID NO: 7

(QVQLQESGPGLVKPSETLSLTCTVSGFSLLSYGVHWVRQPPGKGLEWLGV

IWTGGTTNYNSALMSRFTISKDDSKNTVYLKMNSLKTEDTAIYYCARYYYG

MDYWGQGTLVTVSS)

and the humanized AB0041 light chain variant VH4 (having the light chain sequence set forth in Vk4 (having the sequence set forth in SEQ ID NO: 12

(DIQMTQSPSSLSASVGDRVTITCKASQDVRNTVAWYQQKPGKAPKLLIY

SSSYRNTGVPDRFSGSGSGTDFTLTISSLQAEDVAVYYCQQHYITPYTFG

GGTKVEIK)).

The heavy chain of the AB0045 antibody has the sequence set forth in SEQ ID NO: 49

(MGWSLILLFLVAVATRVHSQVQLQESGPGLVKPSETLSLTCTVSGFSLL

SYGVHWVRQPPGKGLEWLGVIWTGGTTNYNSALMSRFTISKDDSKNTVYL

KMNSLKTEDTAIYYCARYYYGMDYWGQGTLVTVSSASTKGPSVFPLAPCS

RSTSESTAALGCLVKDYFPEPVTVSWNSGALTSGVHTFPAVLQSSGLYSL

SSVVTVPSSSLGTKTYTCNVDHKPSNTKVDKRVESKYGPPCPPCPAPEEF

LGGPSVFLFPPKPKDTLMISRTPEVTCVVVDVSQEDPEVQFNWYVDGVEV

HNAKKPREEQFNSTYRVVSVETVTHQDWENGKEYKCKVSNKGLPSSIEKT

ISKAKGQPREPQVYTLPPSQEEMTKNQVSLTCLVKGFYPSDIAVEWESNG

QPENNYKTTPPVLDSDGSFFLYSRLTVDKSRWQEGNVFSCSVMHEALHNH

YTQKSLSLSLGK (signal sequence underlined sequence of the constant region presented italics)); the light chain of the AB0045 antibody has the sequence set forth in SEQ ID NO: 50

(MRVPAQLLGLLLLWLPGARCDIQMTQSPSSLSASVGDRVTTTCKASQDV

RNTVAWYQQKPGKAPKLLIYSSSYRNTGVPDRFSGSGSGTDFTLTISSLQ

AEDVAVYYCQQHYITPYTFGGGTKVEIKRTVAAPSVFIFPPSDEQLKSGT

ASVVCLLNNFYPREAKQWKVDNALSGNSQESVTEQDSKDSTYSLSSTLTL

SKADYEKHKVYACEVTHQGLSSPVTKSFNRGEC (signal sequence underlined; sequence of the constant region presented italics)).

The antibody contains 1312 amino acids in length, is composed of two heavy chains and two light chains, and has a theoretical pI of about 7.90, extinction coefficient of about 1.50 AU/cm at 280 nm for 1 g/L, a molecular weight of about 144 kDa, and density of about 1 g/mL in formulation buffer (50-100 mg/mL product concentration).

Further characterization of this antibody is described in Example 3, below.

Example 3: Characterization of Variant MMP9 Antibody AB0045 and Comparison to AB0041 and AB0046

As described above, AB0045 and AB0041 antibodies are non-competitive inhibitors of MMP9. Thus, both antibodies inhibit MMP9 enzymatic activity independently of substrate concentration. The AB0045 antibody binds to the same MMP9 epitope as the AB0041 antibody with an affinity in the 1×10-12 molar range, as shown by direct binding and surface plasmon resonance (SPR) assays. Both antibodies are specific for MMP9, with no significant non-specific binding observed against other purified protein targets including purified domains and full length forms of MMP enzymes. Both AB0045 and AB0041 antibodies are cross-reactive with native and recombinant human and recombinant rat and cynomolgus monkey MMP9.

The in vitro binding affinity, inhibition characteristics, and the specificity of the antibodies of AB0045, AB0041 and AB0046 for MMP9 of human and non-human origin were determined using Enzyme-Linked Immunosorbent Assay (ELISA) and an MMP9 enzymatic assay. SPR analysis was also used to generate dissociation constants ($K_d$) of AB0045 and AB0041.

In the ELISA assay, the $K_d$ value of AB0045 and AB0041 antibodies for human, cynomolgus monkey, and rat MMP9 derived from ELISA were all found to be <400 pM. The ELISA data illustrated that both AB0045 and AB0041 antibodies cross-react with MMP9 from all the relevant toxicology species tested. The AB0046 antibody was shown to be specific to mouse MMP9 and therefore could be used as a surrogate antibody in mouse efficacy models. The results showed that the $K_d$ value of the AB0045 antibodies for human MMP9 was 0.168±0.117 nM and the and $K_d$ value of the AB0041 antibody was 0.133±0.030 nM. The results on the AB0046 antibodies showed it bound to mouse MMP9 with the $K_1$ value of 0.218±0.097 nM. In the SPR analysis, the results showed that the $K_d$ values of AB0045 and AB0041 antibodies for human MMP9 were 8.8 pM and 0.4 pM, respectively.

The enzymatic inhibitory activities of AB0045, AB0041, and AB0046 antibodies were evaluated in an assay assessing MMP9-mediated cleavage of a fluorogenic peptide substrate Mca-PLGL-Dpa-AR-NH2. All three antibodies inhibited MMP9 enzyme activity. The $IC_{50}$ values of AB0045 (0.691±0.097 nM) and AB0041 (0.569±0.185 nM) for human MMP9 were not statistically different. The $IC_{50}$ value for the AB0046 inhibition of mouse MMP9 was 0.352±0.03 nM. The value was not adjusted for the concentration of active enzyme that was generated during the preparation. Additional MMP9 enzymatic assay under steady-state conditions was used to determine $IC_{50}$ and mode of inhibition. In this assay, the $IC_{50}$ values of AB0045 ranged from 0.148 nM to 0.161 nM in a 20-fold range of substrate concentration, and in one example is 0.158 nm The results showed that the MMP9 inhibitory activity of AB0045 was non-competitive.

TABLE 2B

Binding and Inhibitory Properties of AB0045, AB0041, and surrogate mouse antibody AB0046

|  | AB0045 | AB0041 | AB0046 |
|---|---|---|---|
| ELISA | | | |
| Human MMP9 Dissociation constant | 0.168 ± 0.117 nM | 0.133 ± 0.030 nM | >100 nM |
| Cynomolgus monkey MMP9 Dissociation constant | 0.082 ± 0.022 nM | 0.145 ± 0.16 nM | >100 nM |
| Mouse MMP9 Dissociation constant | >100 nM | >100 nM | 0.218 ± 0.097 nM |
| Rat MMP9 Dissociation constant | 0.311 ± 0.017 nM | 0.332 ± 0.022 nM | >100 nM |
| SPR | | | |
| Human MMP9 Dissociation constant | 8.8 pM | 0.4 pM | ND |
| Activity Assay | | | |
| Human MMP9 $IC_{50}$ | 0.691 ± 0.097 nM | 0.569 ± 0.185 nM | >100 nM |
| Cynomolgus monkey MMP9 $IC_{50}$ | 0.194 ± 0.048 nM* | 0.189 ± 0.019 nM* | >100 nM |
| Rat MMP9 $IC_{50}$ | 8.23 ± 1.24 nM* | 2.78 ± 1.17 nM * | >100 nM |
| Mouse MMP9 $IC_{50}$ | >100 nM | >100 nM | 0.352 ± 0.03 nM* |

The results confirmed that AB0045 and AB0041 have equivalent binding and inhibitory properties and that AB0046 can serve as a relevant mouse surrogate antibody, for example, in mouse models of human disease.

What is claimed is:

1. An isolated antibody or antigen binding fragment thereof that binds matrix metalloproteinase 9 (MMP9), comprising:
   a heavy chain comprising a heavy chain variable (VH) domain, wherein the VH domain comprises a complementarity-determining region 1 (CDR-H1) comprising the amino acid sequence set forth in SEQ ID NO: 51, a CDR-H2 comprising the amino acid sequence set forth in SEQ ID NO: 52, and a CDR-H3 comprising the amino acid sequence set forth in SEQ ID NO: 53; and
   a light chain comprising a light chain variable (VL) domain, wherein the VL domain comprises a CDR-L1 comprising the amino acid sequence set forth in SEQ ID NO: 54, a CDR-L2 comprising the amino acid sequence set forth in SEQ ID NO: 55, and a CDR-L3 comprising the amino acid sequence set forth in SEQ ID NO: 56.

2. The isolated antibody or antigen binding fragment thereof of claim 1, wherein the VH domain comprises the amino acid sequence of SEQ ID NO: 47.

3. The isolated antibody or antigen binding fragment thereof of claim 1, wherein the VL domain comprises the amino acid sequence of SEQ ID NO: 48.

4. The isolated antibody or antigen binding fragment thereof of claim 1, wherein the VH domain comprises the amino acid sequence of SEQ ID NO: 47, and the VL domain comprises the amino acid sequence of SEQ ID NO: 48.

5. The isolated antibody or antigen binding fragment thereof of claim 1, wherein the VH domain comprises an amino acid sequence having at least about 95%, 96%, 97%, 98%, or 99% sequence identity with the amino acid sequence of SEQ ID NO: 47.

6. The isolated antibody or antigen binding fragment thereof of claim 1, wherein the VL domain comprises an amino acid sequence having at least about 95%, 96%, 97%, 98%, or 99% sequence identity with the amino acid sequence of SEQ ID NO: 48.

7. The isolated antibody or antigen binding fragment thereof of claim 1, wherein the VH domain comprises an amino acid sequence having at least about 95%, 96%, 97%, 98%, or 99% sequence identity with the amino acid sequence of SEQ ID NO: 47; and the VL domain comprises an amino acid sequence having at least about 95%, 96%, 97%, 98%, or 99% sequence identity with the amino acid sequence of SEQ ID NO: 48.

8. The isolated antibody or antigen binding fragment thereof of claim 1, wherein the heavy chain comprises the amino acid sequence set forth in SEQ ID NO: 57.

9. The isolated antibody or antigen binding fragment thereof of claim 1, wherein the light chain comprises the amino acid sequence set forth in SEQ ID NO: 58.

10. The isolated antibody or antigen binding fragment thereof of claim 1, wherein the heavy chain comprises the amino acid sequence set forth in SEQ ID NO: 57, and the light chain comprises the amino acid sequence set forth in SEQ ID NO: 58.

11. A composition comprising the isolated antibody or antigen binding fragment thereof of claim 1.

12. The composition of claim 11, further comprising a pharmaceutically acceptable excipient.

13. A kit comprising the composition of claim 11.

* * * * *